(12) United States Patent
O'Connor et al.

(10) Patent No.: US 9,955,900 B2
(45) Date of Patent: May 1, 2018

(54) SYSTEM AND METHOD FOR CONTINUOUS MONITORING OF A HUMAN FOOT

(71) Applicant: QUAERIMUS, INC., Newark, CA (US)

(72) Inventors: Richard W. O'Connor, Redwood City, CA (US); Alan D. Baldwin, San Jose, CA (US); Chwen-Yuan Ku, San Jose, CA (US); Jivko M. Mihaylov, San Jose, CA (US); David E. Goodman, Greenbrae, CA (US); Lester J. Lloyd, Orinda, CA (US); Joseph A. Heanue, Oakland, CA (US)

(73) Assignee: QUAERIMUS, INC., Newark, CA (US)

( * ) Notice: Subject to any disclaimer, the term of this patent is extended or adjusted under 35 U.S.C. 154(b) by 655 days.

(21) Appl. No.: 13/898,951

(22) Filed: May 21, 2013

(65) Prior Publication Data

US 2014/0121532 A1    May 1, 2014

Related U.S. Application Data

(60) Provisional application No. 61/720,997, filed on Oct. 31, 2012, provisional application No. 61/721,149, filed on Nov. 1, 2012.

(51) Int. Cl.
*A61B 6/00* (2006.01)
*A61B 5/107* (2006.01)
(Continued)

(52) U.S. Cl.
CPC .......... *A61B 5/1074* (2013.01); *A61B 5/0064* (2013.01); *A61B 5/1032* (2013.01);
(Continued)

(58) Field of Classification Search
None
See application file for complete search history.

(56) References Cited

U.S. PATENT DOCUMENTS 4,267,728 A     5/1981  Manley et al.
4,534,365 A  *  8/1985  Bonetta et al. ............... 600/592
(Continued)

OTHER PUBLICATIONS

Dmitry Yudovsky et al., "Assessing diabetic foot ulcer development risk with hyperspectral tissue oximetry," Journal of Biomedical Optics, Feb. 2011, 026009, vol. 16(2), SPIE, USA.
(Continued)

*Primary Examiner* — James Kish

(57) ABSTRACT

A device for monitoring human feet can include: a transmissive sheet configured to bear at least 90 kg supported at a height of no more than 23 cm, and a foot image capture system below the sheet. An optical image sensor can capture a field of view including at least 250 cm² of the surface of the sheet. The device can have a central reflective element positioned below the sheet directly above the sensor and two outer mirrors such that two fields of view at least 250 cm² each can be focused onto the sensor by a lens. Foot sole images can be automatically captured when a patient stands on the device. Images can be transmitted to a database and associated with the patient by analyzing the images for a unique predetermined metric.

16 Claims, 11 Drawing Sheets

(51) Int. Cl.
  *A61B 5/00* (2006.01)
  *A61B 5/103* (2006.01)
  *A61B 5/1174* (2016.01)

(52) U.S. Cl.
  CPC .......... *A61B 5/1036* (2013.01); *A61B 5/1079* (2013.01); *A61B 5/1174* (2013.01); *A61B 5/445* (2013.01); *A61B 5/4851* (2013.01)

(56) References Cited

U.S. PATENT DOCUMENTS

| | | | |
|---|---|---|---|
| 4,858,621 A | 8/1989 | Franks | |
| 5,002,392 A * | 3/1991 | Swope et al. | 356/328 |
| 5,177,802 A * | 1/1993 | Fujimoto | A61B 5/1172 |
| | | | 356/71 |
| 6,031,929 A | 2/2000 | Maitz et al. | |
| 6,205,230 B1 | 3/2001 | Sundman et al. | |
| 6,243,601 B1 * | 6/2001 | Wist | A61B 5/0088 |
| | | | 250/358.1 |
| 6,289,107 B1 | 9/2001 | Borchers et al. | |
| 6,549,639 B1 * | 4/2003 | Genest | A43D 1/025 |
| | | | 382/100 |
| 2004/0115861 A1 * | 6/2004 | Wong et al. | 438/102 |
| 2005/0097762 A1 * | 5/2005 | Biesbrouck | A61B 5/1074 |
| | | | 33/3 R |
| 2007/0016079 A1 * | 1/2007 | Freeman | A61B 5/0059 |
| | | | 600/476 |
| 2007/0211355 A1 * | 9/2007 | Dalbo et al. | 359/871 |
| 2007/0225572 A1 * | 9/2007 | Murillo | A61B 5/0059 |
| | | | 600/247 |
| 2010/0028991 A1 | 2/2010 | McCall | |
| 2010/0165184 A1 * | 7/2010 | Park et al. | 348/374 |
| 2010/0315833 A1 * | 12/2010 | Holman | G02B 6/0028 |
| | | | 362/607 |
| 2011/0255303 A1 | 10/2011 | Nichol et al. | |
| 2012/0109013 A1 | 5/2012 | Everett et al. | |
| 2012/0197137 A1 | 8/2012 | Jeanne et al. | |
| 2012/0236594 A1 | 9/2012 | Parker et al. | |
| 2013/0053677 A1 | 2/2013 | Schoenfeld | |
| 2013/0258085 A1 * | 10/2013 | Leedy | A43D 1/025 |
| | | | 348/77 |
| 2014/0104395 A1 * | 4/2014 | Rohaly | G01B 11/165 |
| | | | 348/47 |

OTHER PUBLICATIONS

Constantijn E V B Hazenberg et al., "Telemedical home-monitoring of diabetic foot disease using photographic foot imaging—a feasibility study," Journal of Telemedicine and Telecare, 2012, 32-36, vol. 18(1), Sage Publications, USA.

* cited by examiner

SYSTEM AND METHOD FOR CONTINUOUS MONITORING OF A HUMAN FOOT

RELATED U.S. APPLICATIONS

This application claims priority to the co-pending U.S. provisional patent application Ser. No. 61/720,997, entitled "System and Method for Prevention of Diabetic Foot Ulcers," with filing date of Oct. 31, 2012, and the co-pending U.S. provisional patent application Ser. No. 61/721,149, also entitled "System and Method for Prevention of Diabetic Foot Ulcers," with filing date of Nov. 1, 2012, both of which are hereby incorporated by reference in their entirety.

FIELD OF THE INVENTION

The present invention pertains to in-home monitoring for diabetic patients. The present invention also pertains to foot imaging devices.

BACKGROUND

Patients that suffer from diabetic neuropathy gradually lose sensing function in their lower extremities, particularly their feet. Yet neuropathic patients can maintain motor function, such that they can continue walking on, e.g., applying pressure and exposing to possible injury, feet for which they may have lost nociception. Nociception is the sensory or neural capacity to recognize adverse or noxious stimuli. With loss of nociception, patients can have an increased risk of developing a serious injury or ulcer on their feet; when a patient does not feel a pressure point or wound as painful or uncomfortable, he or she may not notice an issue before it has progressed to a serious, highly noticeable degree. For example, Diabetic Foot Ulcers (DFU's) may sometimes only be recognized when blood begins to appear on a patient's sock, a point at which ischemia, e.g., tissue death, which started at an internal tissue region has already progressed through tissue to an outer layer, and amputation may be necessary. 15% to 25% of diabetic patients are likely to develop a DFU in their lifetimes. DFU's can lead to hospitalization, amputation, and ultimately a heightened patient morbidity risk.

Regular inspection and analysis of a diabetic patient's feet can help lower the risk of DFU formation and may have other benefits for improving the health of the patient's feet. However, it can be physically difficult for a diabetic patient to view his or her feet, and further difficult for a patient to discern from a cursory view indications of a developing wound. Foot imaging devices have been introduced for shoe-fitting applications, such as determining the appropriate size or insole for an athletic or walking shoe, or advanced clinical use, such as hyperspectral imaging applications. A limited number of devices have been proposed for patient viewing of his or her feet outside of a clinic. However, none of the existing devices provide sufficient information for analysis of the health of a patient's foot or a structure that is suitable for in-home use.

What is needed is a device suitable for in-home use and providing sufficient monitoring of the health of a patient's feet, particularly to avoid the development of diabetic foot ulcers.

SUMMARY

The present invention pertains to a device and method for monitoring of human feet including a transmissive sheet configured to bear at least 90 kg supported at a height of no more than 23 cm and an image capture system below the sheet wherein an optical image sensor can capture a field of view including at least 250 $cm^2$ of the surface of the sheet. The sheet may also be positioned at a height of no more than 5 cm. The image capture system can also comprise one or more diffuse optical sources and an array of at least four optical imaging sensors with lenses configured to each focus a unique predetermined portion of the field of view onto the sensor to which it is coupled, such that a processing unit can reconstruct a final image from the portions. The device may also have two angled outer mirrors each reflecting half of the field of view towards the center of the device. A central support can rotate an imaging sensor between the two different positions, or two imaging sensors can be utilized. An additional light source can be configured to emit light into the sheet for total internal reflection. One or more additional light sources may emit light with wavelengths between 750 nm and 900 nm, and a lens configured to focus light of at least two unique wavelengths, of which one is between 390 nm and 710 nm and the other is between 750 nm and 900 nm, onto a single focal plane can be provided. The sheet can be glass that does not have anti-reflection treatment.

A device with two outer mirrors can also have a central reflective element positioned below the sheet directly above the sensor such that two fields of view at least 250 $cm^2$ each can be reflected onto the central reflective element by the outer mirrors and focused onto the sensor by a lens. The two fields of view can be separated by at least 10 cm, and a light source can be positioned such that the vertical projection of the source position into the plane of the transmissive sheet is outside of the fields of view. The optical distance between the central reflective element and lens may be fixed by a support structure. An outer mirrors can be positioned with an angle from the transmissive sheet between 8 degrees and 45 degrees, inclusive, or less than 40 degrees.

Foot sole images can be automatically captured with visible light when the patient stands on the device. Images can be transmitted to a database and can be associated with a patient by analyzing the images for a unique predetermined metric. Additional images can be captured using near-infrared light or total internal reflection imaging. A wireless transmitter can be utilized to transmit the image data to the database.

These and other objects and advantages of the various embodiments of the present invention will be recognized by those of ordinary skill in the art after reading the following detailed description of the embodiments that are illustrated in the various drawing figures.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

Embodiments of the present invention may comprise devices, systems, and methods for monitoring or evaluating the feet of diabetic, neuropathic, or other patients for injuries, ulcers, developing ulcers, or similar conditions. These embodiments may collect data or images for viewing or analysis by a medical practitioner or patient. Embodiments may also comprise analysis functions and alert medical practitioners or patients upon detection of an injured, ulcerated, or at-risk site on a patient's foot. Data or images collected by embodiments of the present invention can also serve other preventative and diagnostic functions. For example, embodiments may comprise devices tailored to in-home or medical office use for examining tissue or extremity health monthly, weekly, daily, or more frequently. Such monitoring devices may image a patient's feet or may measure a parameter relevant to tissue or extremity health including but not limited to tissue perfusion, temperature, moisture, or pressure load.

In one embodiment of the present invention, a monitoring device can comprise an image capture system configured to image the bottom of a patient's foot or feet. The bottoms or soles of a patient's feet can be particularly difficult to see without assistance, increasing the likelihood of an undetected injury or site of ulcer development. The bottoms or soles of a patient's feet can also be particularly susceptible to injury or ulceration from the pressure loads applied during walking, standing, and other activity.

Figure 1:
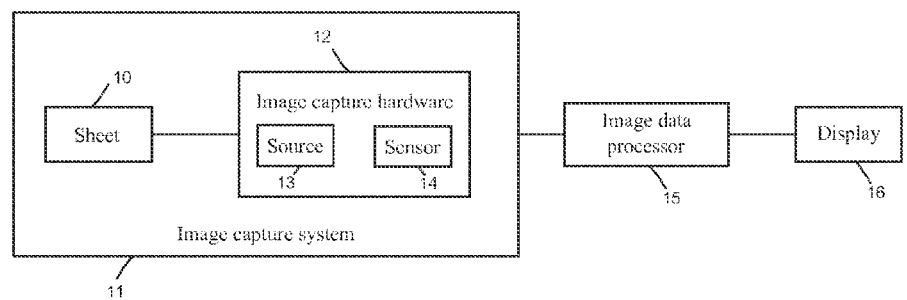
FIG. 1 is a diagram representing a periodic monitoring device of an embodiment of the present invention configured to image the bottoms, e.g., sole or soles, of a patient's feet.

FIG. 1 is a diagram representing a periodic monitoring device of an embodiment of the present invention configured to image the bottoms, e.g., sole or soles, of a patient's feet. A sheet 10 may be configured to support a patient's weight such that the embodiment can be utilized to acquire images of a loaded patient foot, e.g., with the patient standing on sheet 10. An image capture system 11 can be configured to capture an image or images of tissue that is near or in contact with sheet 10.

Image capture system 11 can comprise image capture hardware 12, which may include one or more optical sources 13 and one or more optical sensors 14. Source 13 can emit electromagnetic radiation including but not limited to visible light or near-infrared light. For example, source 13 may emit light of wavelengths between 350 nm and 1 µm, inclusive. Alternatively, source 13 may emit light of wavelengths between 380 nm and 750 nm, 750 nm and 1 µm, or 850 nm and 1550 nm, inclusive, or any other ranges within the enumerated values. Optical source 13 may be a light-emitting diode (LED), laser, cold cathode fluorescent lamp (CCFL), xenon lamp, other type of lamp, or any other type of optical source.

Image capture hardware 12 may further comprise mirrors, including but not limited to plane, concave, convex, or parabolic mirrors; lenses, including but not limited to spherical, non-spherical, concave, convex, planar, compound, gradient-indexed, or wide-angle lenses; prisms; gratings; polarizers; or other optical hardware for focusing, redirecting, or otherwise affecting light emitted by source 13. Image capture hardware 12 can be configured to focus in a plane at the top of or above sheet 10. Image capture hardware 12 may further be configured to achieve a depth of field (DOF) with a range of at least 1.25 cm, e.g., extending from the top surface of sheet 10 to a plane at 1.25 cm above sheet 10. For example, embodiments of the present invention may have a DOF between 1.25 cm and 2.54 cm, 1.6 cm and 2.54 cm, 1.9 cm and 2.54 cm, 2.22 cm and 2.54 cm, or of approximately 2.5 cm, above sheet 10.

In one embodiment of the present invention, depth of field may be sharply truncated past the desired range, e.g., to avoid imaging other body parts, objects in the room, or anything other than the patient's feet. This truncation may be accomplished by selection of lenses with a sharp drop-off in depth of field, or alternatively during image reconstruction or processing. For example, background subtraction, saturation value thresholds, or other image processing techniques may be utilized.

Sheet 10 can be a non-opaque or transmissive material including but not limited to glass, tempered glass, float glass, safety glass, polycarbonate, plastic, or any combination or hybrid thereof. In one embodiment of the present invention, glass or any type of modified glass can be utilized for a particularly scratch-resistant sheet. Scratch resistance may enhance the durability and imaging quality of an image capture system of embodiments of the present invention. Scratch resistance may also or alternatively be enhanced by a scratch-resistant coating, including but not limited to a diamond-like carbon (DLC), polycrystalline diamond film, or other scratch-resistant, transparent coatings, or by scratch-resistance treatments such as ion exchange processes or treatments.

In a further embodiment of the present invention, glass with a low iron content can be utilized for sheet 10. Iron oxide left in glass by the raw materials used during production can affect the color of light passing through the glass, e.g., cause a slightly green appearance, and can impact light transmission. The effects of iron oxide content can increase with glass thickness. As the thickness of sheet 10 may be sufficiently large to support a wide range of patient body weights, a low-iron glass sheet in this embodiment of the present invention may provide measurable clarity and color-accuracy advantages. Transmittance of a low-iron glass sheet in this embodiment may be, for example, at least 87%, 88%, 89%, 90%, or 91%, inclusive, or have any integer or non-integer transmittance value between or above the enumerated percentages.

Sheet 10 may also comprise anti-reflective glass or have an anti-reflective coating, e.g., in a manner to reduce specular reflection during image capture. However, in many embodiments of the present invention, imaging configurations can be utilized that reduce the need for anti-reflective glass or coatings. As described in greater detail below, these embodiments can be configured in a manner to remove paths of specular reflection between light sources and sheet 10 from the field of view of an imaging sensor. Alternatively, polarizers can be utilized to cancel light that has undergone specular rather than diffuse reflection. Elimination of a need for anti-reflective glass or coatings can reduce costs of manufacturing embodiments of the present invention.

Thickness of sheet 10 in embodiments of the present invention may be between 0.32 cm and 2.54 cm, inclusive, and any integer or non-integer thickness between the enumerated values. Thickness of sheet 10 may further be between 0.3 cm and 1.25 cm, inclusive. For example, thickness of sheet 10 may be 0.3 cm, 0.32 cm, 0.79 cm, 0.8 cm, 0.9 cm, 0.95 cm, 1.1 cm, 1.11 cm, 1.2 cm, or 1.25 cm. The material and thickness of sheet 10 can be tailored to accommodate a weight or range of weights. For example, embodiments of the present invention may be tailored to accommodate weights up to 90 kg, 115 kg, 135 kg, 160 kg, 180 kg, 200 kg, or 225 kg, or any other weight below or between the enumerated values.

Sheet 10 can have an area between 515 square centimeters ($cm^2$) and 3225 $cm^2$, inclusive. Sheet 10 can further have an area between 950 $cm^2$ and 3000 $cm^2$, 1300 $cm^2$ and 2600 $cm^2$, 1600 $cm^2$ and 2250 $cm^2$, or 2000 $cm^2$ and 2200 $cm^2$, inclusive, and any other integer or non-integer area within the enumerated ranges. This area can be configured to accommodate one or both of a patient's feet. For example, the area of sheet 10 may be distributed in one sheet accommodating both feet, in two small sheets each accommodating one foot, or in a single sheet accommodating a single foot at a time. In the lattermost embodiment, a solid platform may be positioned at an equal stand-over height as sheet 10, e.g., such that the patient may stand with equal pressure on both feet during imaging.

Sheet 10 can be a rectangular, square, oval, circular, polygonal, or sole-like shape. In an embodiment of the present invention comprising a rectangular sheet, a short dimension of the sheet may be between 25 cm and 50 cm, 28 cm and 45 cm, 30 cm and 40 cm, or 33 cm and 38 cm, inclusive, or any integer or non-integer length within the enumerated ranges. For example, a short dimension of the sheet may be 30.48 cm, 34.29 cm, 35 cm, 35.5 cm, 14.9 cm, and so forth. A long dimension of the sheet in this embodiment may be between 0.3 meters and 1.2 meters, inclusive. A long dimension may further be between 50 cm and 100 cm, 53 cm and 89 cm, 56 cm and 76 cm, or 58 cm and 64 cm, inclusive, or any integer or non-integer length within the enumerated ranges. For example, a long dimension of a rectangular sheet may be 59.7 cm, 60.71 cm, 60.96 cm, 62 cm, and so forth.

Image capture system 11 may be configured such that sheet 10 can be positioned at a convenient height from the ground for a patient to step onto or off of For example, in embodiments of the present invention sheet 10 may be positioned less than 31 cm off the ground. Sheet 10 may further be positioned less than 23 cm, 21 cm, 18 cm, 15 cm, 13 cm, 10 cm, 8 cm, 6 cm, 5 cm, or 3 cm from the ground, inclusive, and any other integer or non-integer height between or below the enumerated values. A convenient stand-over height of image capture systems in embodiments of the present invention may improve patient adherence to regular monitoring, decrease risk of use-related injury, and maintain an aesthetic, low profile for storage in a patient's home. Image capture hardware 12 may be positioned below, in a shared plane with, or in another orientation relative to sheet 10.

Sheet 10 may be supported at any of the enumerated heights in one of a variety of manners. In one embodiment, sheet 10 can be supported by a plurality of legs of a material including but not limited to aluminum, glass, stainless steel, wood, or other materials configured to support a predetermined patient weight. A support leg may be connected to sheet 10 at or near each corner of a polygonal-shaped sheet, e.g., four legs of a square or rectangular sheet, or distributed in an even or predetermined pattern around the circumference of a circular, elliptical, or sole-like sheet. A socket-like connection can be created between sheet 10 and legs, e.g., by matching holes in sheet 10 to narrowed ends of the legs such that sheet 10 sits on top of the legs and is secured against lateral motion; through intermediate mounting attachments, e.g., clamps connection the legs to corners or any edges of sheet 10; or similar connections. Edges of sheet 10 may be chamfered, e.g., for aesthetics and safety. Panels, e.g., walls or housing, may be positioned between support legs configured to occlude light from reaching optical hardware from lateral directions.

Alternatively, other housing configurations may be utilized to support sheet 10. For example, a single-piece construction may support sheet 10 while providing aforementioned occlusion and, optionally, a base or floor below sheet 10. Legs, housing, and other hardware may be configured to avoid optical interaction with sheet 10 or optical hardware 12. For example, legs or housing may be darkly colored, via paints, pigments, or natural composition, or otherwise non-reflective. In one embodiment of the present invention, inner surfaces of housing can be configured to diffusely reflect light.

In an alternative embodiment of the present invention, transmissive sheet 10 may be positioned co-planar with the floor of a patient's home or a clinical office, e.g., may have a stand-over height of 0 cm. To achieve a 0 cm stand-over height, a section of the floor, such as a bathroom tile or tiles, may be replaced with transmissive sheet 10. Image capture hardware 12 may be positioned in a vacated volume below sheet 10, e.g., below the plane of the floor.

In the embodiment of FIG. 1, an image data processor 15 can be located in shared packaging or housing with image capture system 11 or may be an external device coupled to image capture system 11. In the former case, image data processor 15 may comprise one or more microprocessors, microcontrollers, logic chips, integrated circuits, including but not limited to digital integrated circuits, analog integrated circuits, mixed-signal integrated circuits, and memory-integrated circuits, or other computing, processing, or memory chips. In the latter case, image data processor 15 may be implemented in any external computing or processing device, including but not limited to personal computers, smart phones, tablets, or other electronic devices. In an alternative embodiment of the present invention, image processing can be implemented via cloud computing, or any other remote server, network, wireless network, or similar structure.

Coupling between image capture system 11 and image data processor 15 may be physical or wireless. Data can be transmitted from image capture system 11 to an external processor or computing network via a wireless internet connection, a cellular network connections, e.g., 3G, 4G, or similar, or any other type of wireless network connection. Alternatively, data can be transmitted through physical means including but not limited to Ethernet, IEEE 1394 interface, serial, or USB connections.

Images or other information acquired by image capture system 11 or generated by image data processor 15 may displayed, e.g., to a patient, on a display 16. Display 16 can be a liquid crystal display (LCD), thin film transistor LCD (TFTLCD), light-emitting diode (LED), LED-backlit LCD, plasma display panel (PDP), or any other type of polychromatic or monochromatic displays. Alternatively, display 16 can be a patient or medical practitioner's computer, smart phone, tablet personal computer, or other electronic device. In another embodiment of the present invention, multiple imaging modalities can be incorporated in a single apparatus.

Figure 2:
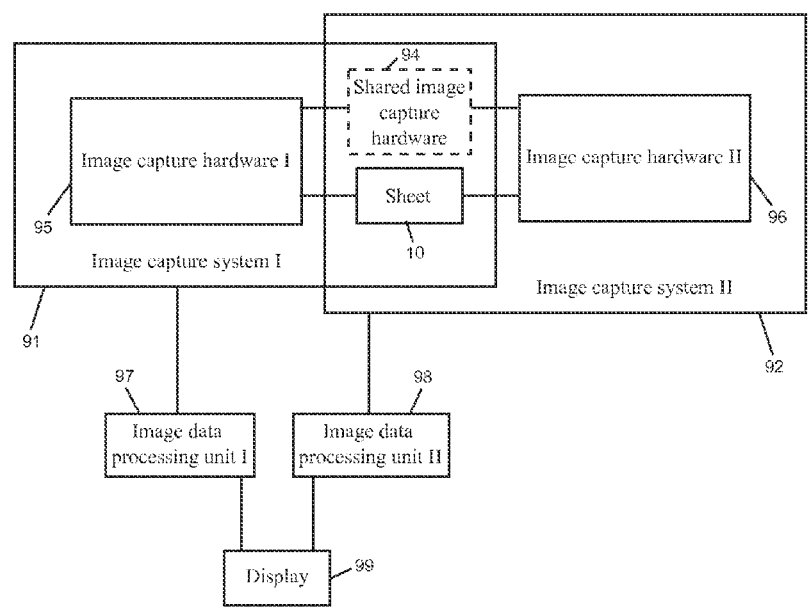
FIG. 2 is a diagram representing a monitoring device comprising multiple image capture systems of an embodiment of the present invention.

Embodiments of the present invention can comprise multiple image capture systems, which can provide additional views or information pertaining to tissue health in a patient. Such embodiments can replicate each element of the embodiment of FIG. 1, e.g., within shared housing or a compact unit, or can share elements. FIG. 2 is a diagram representing a monitoring device comprising multiple image capture systems of an embodiment of the present invention. A first image capture system 91 and second image capture system 92 can share common sheet 10. First image capture system 91 and second image capture system 92 may also optionally share additional elements of image capture hardware 94. Shared image capture hardware 94 may include, for example, a sensor or sensors, source or sources, or other optical elements. First image capture system 91 can further include a set of image capture hardware 95, with second image capture system 92 including another set of image capture hardware 96. These sets can also include a source or sources, sensor or sensors, or other optical elements including but not limited to lenses, mirrors, gratings, and similar elements.

First image capture system 91 can be coupled to a processing unit 97 for reconstructing or processing image data. Similarly, second image capture system 92 can be coupled to a processing unit 98 for reconstruction or processing. First processing unit 97 and second processing unit 98 may be implemented in separate processors or in a single processor. Final images may be displayed separately or overlaid or otherwise combined. Display 99 may comprise one or two panels to display separate, combined, or otherwise related final images. Image processing or image data processing from the two image modalities can be analyzed separately or in conjunction with one another for determination of injured, ulcerated, or at-risk sites on a patient's foot.

In one embodiment of the present invention, data acquired by a periodic monitoring device, e.g., the periodic monitoring device of FIG. 1, FIG. 2, or other devices, may be added, linked, or sent to an electronic medical record (EMR). Data from multiple types of measurements may optionally be aggregated before, during, or after addition to the EMR. Data may be aggregated and may be linked to the EMR by any physical or wireless means, including but not limited to a cloud computing interface or other server interface. Data aggregation may be performed between data acquired from one or multiple monitoring devices, measurements performed during visits with a medical practitioner, or any other modes of patient data collection. These data and measurements can include without limitation tissue temperature, tissue perfusion, patient weight, pulse, heart rate, respiratory rate, localized pressure loading, pressure loading patterns, degree of neuropathy, locations of known physical deformities or other conditions, history of injury or ulceration, or any other metrics or conditions related to tissue and patient health.

Figure 3:
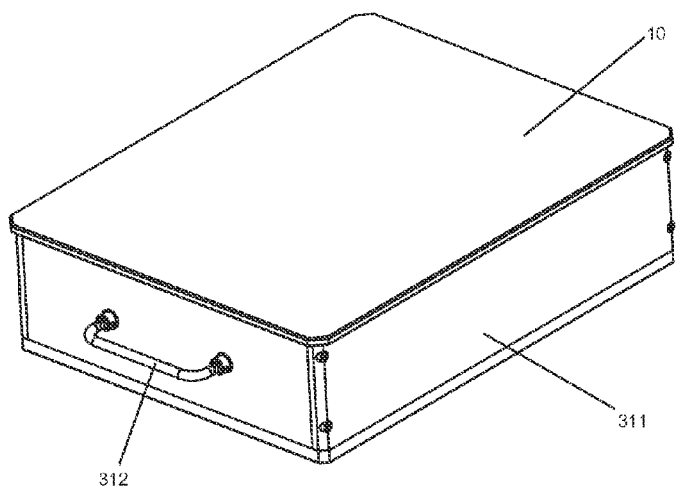
FIG. 3 is a diagram representing an embodiment of the present invention wherein imaging hardware can be fully contained and portability features provided.

The embodiments of FIG. 1, FIG. 2, and similar embodiments and implementations thereof may be low-profile, portable, or otherwise tailored to in-home use. FIG. 3 is a diagram representing an embodiment of the present invention wherein imaging hardware can be fully contained and portability features can be provided. An image capture system or systems, e.g., according to the embodiments of FIG. 1 or FIG. 2, can be provided within housing 311. One or more handles 312 may be attached to housing 311 and may facilitate lifting or moving of the device. Optionally, wheels may be provided on the bottom of the device such that the device may be rolled between locations of use.

The stand-over height of the embodiment of FIG. 3 can also be particularly suited to in-home use, e.g., allowing a patient to easily step on or off the device with little or minimal assistance. For example, the stand-over height of the embodiment of FIG. 3 can be equal to or less than 23 cm. The stand-over height of the embodiment of FIG. 3 can further be between 18 cm and 6 cm, 17 cm and 9 cm, or 16 cm and 12 cm, inclusive, and any other integer or non-integer number of centimeters within or between the enumerated ranges. Systems and methods of embodiments of the present invention that may provide these stand-over heights are described in greater detail below.

Figure 4:
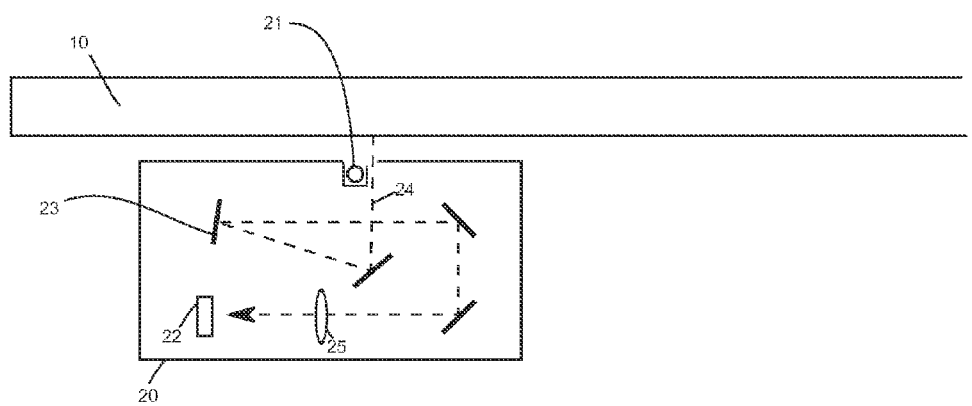
FIG. 4 is a diagram illustrating a scanning image capture system of one embodiment of the present invention.

FIG. 4 is a diagram illustrating a scanning image capture system of one embodiment of the present invention. Scanning element 20 may be located directly below sheet 10 and can be scanned across sheet 10 by mechanical components including without limitation a motor, e.g., a stepper motor; belt; stabilizer bar; or other actuating or stabilization elements. A scanning element 20 may carry a source 21 and a sensor 22. Scanning element 20 may also carry mirrors, lenses, or other optical hardware. For example, in the embodiment of FIG. 4, mirrors 23 or other optical elements may be utilized to direct light scattered by tissue in contact with sheet 10 toward sensor 22. A lens or lenses 25 can focus light onto the sensor 22.

Sensor 22 can comprise, without limitation, a CCD image sensor, e.g., CCD array, or complementary metal-oxide semiconductor (CMOS) image sensor. Source 21 can comprise LED's, lasers, lamps, or other light sources. Source 21 may extend across scanning element, e.g., as a lamp or linear array of LED's, or may be positioned on either or both ends of scanning element 20. In the latter case, a reflective element may be positioned across scanning element 20 in a manner to illuminate sheet 10 uniformly across the length of scanning element 20.

Contemporary flatbed or document scanners can utilize contact image sensors (CIS), which may comprise a CCD array physically coupled to an imaging surface by an optical element such as a gradient-indexed (GRIN) lens. However, thickness of the transmissive sheet in a CIS-based scanner can be between 1 mm and 5 mm; these transmissive sheets may only need to support the weight of documents, books, or similarly light materials, in contrast to the weight of a human as can be supported by embodiments of the present invention. The focal length of a GRIN lens in a CIS-based scanner may be related to or matched to the thickness of the sheet, e.g., 1 mm to 5 mm, and may provide a depth of field extending up to approximately 0.5 mm above the sheet. In contrast, embodiments of the present invention may utilize transmissive sheets of thickness greater than 7 mm and achieve a depth of field encompassing at least 13 mm above the transmissive sheet.

Scanners of embodiments of the present invention may be operated without full coverage of the transmissive sheet, e.g., without a lid or cover occluding ambient and stray light from entering the transmissive sheet. Scanners of the present invention may allow regions of the image, e.g., those not covered by patient tissue, to become saturated, e.g., rather than implementing gain control to avoid saturation. Images of the feet can be isolated from a saturated or unsaturated background during processing. This may be accomplished by feature recognition, a saturation threshold, or any other background subtraction method. These embodiments may be configured handle a wide range of ambient or stray light situations.

Scanning element 20 may extend across a short dimension of sheet 10, e.g., to minimize amounts of imaging hardware and manufacturing cost, or across a long dimension of sheet 10, e.g., to minimize scanning time. Length of scanning element 20 may be equal to the dimension of sheet 10, e.g., between 25 cm and 125 cm, inclusive, or less than the dimension of sheet 10 by a predetermined amount, e.g., to accommodate mechanical hardware or housing. Sources, sensors, and other optical elements may extend across the full length of scanning element 20, or may be centered or otherwise distributed on scanning element 20. Multiple scanning elements may also be utilized and each scan discrete regions of sheet 10.

An image may be reconstructed from image data acquired during a single scan of scanning element 20 across sheet 10. Alternatively, scanning element 20 may scan across sheet 10 multiple times, and an image may be reconstructed from aggregated, averaged, or otherwise combined data. One, two, three, four or more scans may be completed and utilized for image reconstruction or analysis. Each scan may be completed with the same wavelengths of light, e.g., a broadband or white light source, or one of a sequential set of wavelengths, e.g., a combination of red, green, blue, infrared, near-infrared, or any other wavelength sources.

Figure 5:
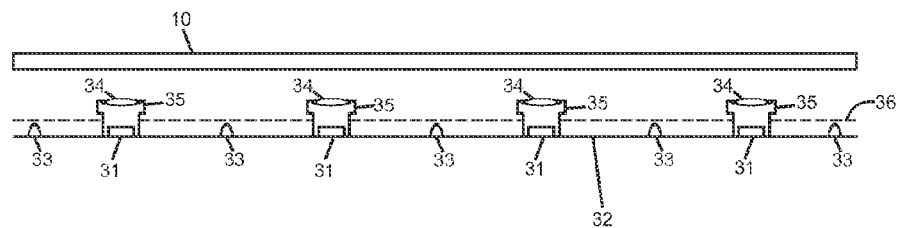
FIG. 5 is a diagram illustrating an image capture system comprising a static sensor array of an embodiment of the present invention.

FIG. 5 is a diagram illustrating an image capture system comprising a static sensor array of an embodiment of the present invention. In this embodiment, an array of sensors 31 may be positioned in a plane below sheet 10. A divergent source or sources 33 may be positioned in the same or a different plane to illuminate sheet 10. A lens or lenses 34 may be positioned over each sensor 31 of the array. Lenses may be positioned and secured above sensors 31 by lens mounts 35 or other hardware components. Lens mounts 35 may be opaque and may shield sensors 31 from direct radiation from sources 33. Lens mounts 35 may have a height sufficient to prevent direct radiation from sources 33 being incident on lenses 34. The height of lens mounts 35, e.g., distance of lenses 34 from the plane with sources 33, may, for example, be greater than 0.6 cm, 0.8 cm, 1.25 cm, or 2.54 cm, or any other integer or non-integer height between the enumerated values.

A diffusive layer 36 may optionally be included above sources 33 but below lenses 34. Diffusive layer 36 may be a light-diffusing material such as powder-coated glass, semi-opaque glass, opaque glass, white opaque plastic, or similar materials. Thickness of diffusive layer may be dependent on the selected material and may be between 0.25 cm and 1.25 cm, inclusive. Thickness of the diffusive layer 36 may further be between 0.3 cm and 0.65 cm, inclusive. Holes or orifices in diffusive layer 36 may be tailored to accommodate lens mounts 35 or lenses 34, e.g., such that lens mounts 35 can protrude through and lenses 34 can be positioned above diffusive layer 36. Diffusive layer 36 may increase the uniformity of illumination of surface 10, and allow greater flexibility in the positioning of sources 33.

Sensors 31 may be CMOS sensors, charge-coupled devices (CCD), or any other type of pixelated optical sensors. Sensors 31 may be square, rectangular, circular, polygonal, or any other shape. If square or rectangular, sensors 31 may have sides of a length between 0.2 cm and 1.25 cm, inclusive, and any fractional length between the enumerated values. For example, square or rectangular sensors may have sides of 0.2 cm, 0.5 cm, 0.65 cm, 0.95 cm, 0.85 cm, and so forth. If circular or polygonal, sensors may have diameters of the aforementioned dimensions.

Sources 33 and sensors 31 may be mounted on a printed circuit board (PCB), turret board, or other type of supporting platform. The platform 32 may be supported by housing shared with sheet 10, e.g., legs, walls, panels, or similar elements. Platform 32 may be secured to the housing by brackets; rest on shelves or pegs, e.g., at the corners of housing or legs; or be positioned below sheet 10 in any other manner. Alternatively, in one embodiment of the present invention, platform 32 can be connected to or suspended from sheet 10. Connecting platform 32 to or suspending platform 32 from sheet 10 can secure a spatial relationship between platform 32 and sheet 10, e.g., such that spatial relationships between optical hardware on platform 32 and sheet 10 are maintained even in case of housing deformations or other mechanical shifts. A secured spatial relationship between platform 32 and sheet 10 may improve device calibration and image reconstruction capabilities. Suspension of platform 32 may also protect sources 33 and sensors 31 from impact, mechanical shocks, and moisture from the ground or floor. Platform 32 can be suspended from sheet 10 by rods, pegs, beams, or similar structures, e.g., secured to holes in or corners of platform 32 and sheet 10.

Sources 33 and sensors 31 may be positioned, e.g., platform 32 may be suspended, less than 31 cm below sheet 10. A convenient stand-over height may be maintained. Additionally, hardware and components for image collection, processing, communication, or other system applications can be housed beneath platform 32 in these embodiments. The sources and sensors may further be positioned less than 23 cm, 18 cm, 15 cm, 13 cm, 10 cm, 8 cm, 6 cm, 5 cm, or 3 cm, or any other integer or non-integer distance between the enumerated values below sheet 10.

Figure 6:
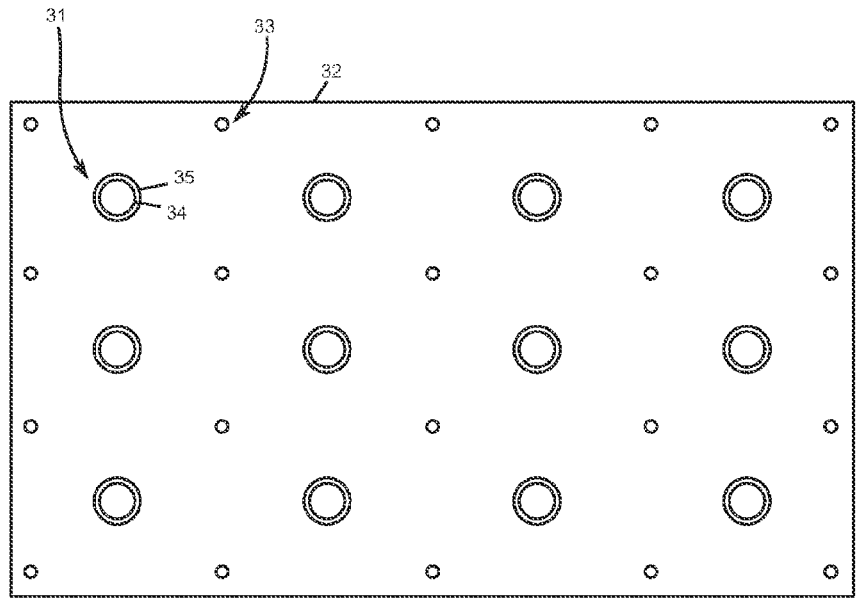
FIG. 6 is a diagram illustrating a static sensor array of an embodiment of the present invention.

FIG. 6 is a diagram illustrating a static sensor array of an embodiment of the present invention. In the embodiments of FIG. 5 and FIG. 6, sources 33 and sensors 31 can be configured to image tissue near or in contact with any area of sheet 10. As previously described, dimensions of sheet 10 may each be between 15 cm and 125 cm, inclusive. In one embodiment the dimension intended to accommodate the length of patients' feet can be between 25 cm and 46 cm, 31 cm and 41 cm, or 33 cm and 38 cm, inclusive, or any other integer or non-integer number of centimeters within or between the enumerated ranges. For example, this dimension may be 31 cm, 31.75 cm, 32 cm, 33.65, 33.86, 35 cm, 35.5 cm, and so forth. In this embodiment a second dimension can be designed to accommodate the width of both of a patient's feet plus the distance between them in a stance comfortable or usual for the patient. This dimension may be between 25 cm and 77 cm, 38 cm and 63.5 cm, 45 cm and 56, or 48 cm and 54 cm, inclusive, or any other integer or non-integer number of centimeters within or between the enumerated ranges. For example, this dimension may be 48.26 cm, 49.53 cm, 50 cm, 51.44 cm, 51.64 cm, 52.7 cm, or 53.35 cm, and so forth.

A number and positioning of sources 33 and sensors 31 in the embodiments of FIGS. 5 and 6 may be configured such that less than 25%, 20%, 15%, 14%, 13%, 12%, 11%, or 10% overlap may exist between image data sets of neighboring sensors.

In one embodiment, this can in part be achieved by use of wide-angle lenses 34, which may provide up to a 120-degree field of view in one or more directions. Wide-angle lenses 34 may further provide a field of view of 70 to 120 degrees, 80 to 100 degrees, or 85 to 95 degrees, inclusive, and any integer or non-integer number of degrees within the enumerated ranges. For example, specialized lenses 34 may provide an 85, 86, 87, 88, 89, 90, 91, 92, or 93 degree field of view around a central axis.

A subset of the area of sheet 10, e.g., a "patch," imaged by each of sensors 31 coupled to one of lenses 34 can be related to the distance of lenses 34 below sheet 10. Patch area may, for example, increase with distance between lenses 34 and sheet 10. Patch area may be between 6.5 cm$^2$ and 130 cm$^2$, inclusive, or further may be between 50 cm$^2$ and 105 cm$^2$, 60 cm$^2$ and 100 cm$^2$, 65 cm$^2$ and 90 cm$^2$, or 70 cm$^2$ and 85 cm$^2$, inclusive, and any integer or non-integer area within the enumerated ranges.

A distance implemented between lenses 34 and sheet 10 may be related to the minimum object distance (MOD) of lenses 34. The MOD of a lens can determine the minimum distance an object must be located from the lens to be in focus in a final image. The MOD of lenses in this embodiment may be between 3 cm and 10 cm, inclusive. The MOD of lenses may further be between 3 cm and 8 cm, 3.5 cm and 7 cm, or 4 cm and 6 cm, inclusive, and any integer or non-integer distance within the enumerated ranges. For example, the MOD of lenses 34 may be 4.5 cm, 4.88 cm, 5 cm, 5.10 cm, and so forth.

Sources 33 in this embodiment may be any of the source types that have been listed previously, including but not limited to LED's, lamps, or other optical sources. Sources 33 may emit light diffusely or be otherwise configured to uniformly illuminate sheet 10. In one embodiment of the present invention, sources 33 can comprise white LED's. In another embodiment of the present invention, inner surfaces of the device, e.g., the top of platform 32, inner surfaces of housing, or other opaque surfaces below sheet 10 may be diffusely reflective white surfaces. This can increase the uniformity of illumination in embodiments of the present invention.

Sources and sensors can be arranged in any one of a large variety of possible configurations. In the embodiment of FIG. 6, sensors 31 are organized in a rectangular array, and sources 33 are regularly interspersed between sensors 31. In this embodiment, an array of sensors may comprise between 1 and 20 elements in each row and column, inclusive. A sensor array may further comprise between 2 and 15 elements, 3 and 10 elements, or 4 and 8 elements in each row and column. Rows and columns may or may not be of equal number of elements, and a difference in elements between rows and columns may be 1, 2, 3, 4, 5, or 6 elements, or in some cases may be greater. For example, arrays of sources or sensors of the present embodiment may comprise 2×2 elements, 2×3 elements, 2×4 elements, 2×5 elements, 2×6 elements, 2×7 elements, 2×8 elements, 3×3 elements, 3×4 elements, 3×5 elements, 3×6 elements, 3×7 elements, 3×8 elements, 3×9 elements, 4×4 elements, 4×5 elements, 4×6 elements, 4×7 elements, 4×8 elements, 4×9 elements, 4×10 elements, 5×5 elements, 5×6 elements, 5×7 elements, 5×8 elements, 5×9 elements, 5×10 elements, 5×11 elements, 6×6 elements, 6×7 elements, 6×8 elements, 6×9 elements, 6×10 elements, 6×11 elements, 6×12 elements, or any other similar such size.

Other configurations and variations of sources and sensors are possible. For example, sources and sensors may be distributed in a manner other than rectangular rows and columns. Sources may be clustered around sensors, be distributed less frequently between sensors, positioned in a different plane than sensors, or in another configuration. Use of auto gain control or variable exposure times may result in acquisition of relatively dark image patches by a given sensor or sensors due to the variability of potential lighting environments where these embodiments may be utilized. In one embodiment of the present invention, the exposure time of each sensor can be fixed at an equal, predetermined length. In this embodiment, a sensor or sensors positioned near a strong stray-light source such as a bathroom or clinical office light may not truncate exposure before collecting a sufficient amount of scattered photons that provide image data.

Sensors in these embodiments may acquire image data simultaneously, sequentially, in sets, or similar manners. In one embodiment, sensors can acquire image data simultaneously. In another embodiment sensors can acquire data according to a predetermined pattern or sequence, including but not limited to a raster, row-by-row, column-by-column, diagonal, circular, or serpentine pattern or sequence. Alternatively, the sources can be activated according to a round-robin or other scheduling or queuing algorithm. A microcontroller, microprocessor, logic chip, external processor coupled to the image capture system, or other processing unit can execute one or more of these patterns or algorithms.

Wide-angle lenses in embodiments of the present invention, in possible conjunction with relatively short distances between sensors and the transmissive sheet, can cause significant distortion in raw image data. In one embodiment of the present invention this type of distortion may be corrected with optical hardware, such as a non-distorting or low distortion wide-angle lens or an additional lens positioned between a wide-angle lens and sensor and configured to remove the distortion. In another embodiment of the present invention, distortion can be corrected post-acquisition, e.g., during image data processing or reconstruction. If other distortions or artifacts arise, e.g., from misalignment between the optical axis of a lens and center of a corresponding sensor, tilt of a lens, non-ideal feature of a lens surface, color bias of a sensor, or other sensor features, such distortions may also be accounted for by device calibration or other image processing techniques.

Another aspect of the present embodiment may comprise combination of multiple image data sets into one or more final images, e.g., combination of image data or "patches" from the plurality of sensors 31 into a final image of two foot soles or a final image of each foot sole. Registration of or determination of spatial relationships between image data sets, e.g., patches, from a sensor array can be determined pre-acquisition, such as through a calibration or analytical process, or during image processing, such as via feature recognition and matching or other image stitching methods.

In one embodiment of the present invention, registration of patches of sheet 10 imaged by sensors 31 can be determined during calibration, e.g., a manufacturing-stage calibration, of the apparatus. The calibration process may include, for example, imaging one or more grids or calibration images and mapping resultant image data sets to said calibration images. Determined relationships or mapping coefficients can be stored in internal or external memory and implemented during subsequent image reconstructions. Other calibration or registration techniques may be utilized. Alternatively, registration and image stitching can be determined or implemented during image processing, such as via feature matching, summing of absolute differences (SAD), or other image stitching methods.

In the embodiment of FIGS. 5 and 6, an array of CMOS or CCD sensors may acquire image data in as little as 0.033 seconds, e.g., if sensors 31 acquire image data sets simultaneously with an image acquisition speed of 30 frames per second (fps). Even if sensors 31 capture image data sequentially, sheet 10 can still be imaged in less than 1 s, 0.9 s, 0.8 s, 0.7 s, 0.6 s, 0.5 s, 0.4 s, 0.3 s, or 0.2 s, inclusive. Embodiments of the present invention can be powered by one of a variety of means, including but not limited to battery, AC power, e.g., electrical plug, or other power supply. Embodiments comprising an electrical plug or a connection to another large external power source may most efficiently acquire image data simultaneously, whereas battery-powered embodiments may optimize battery size and device efficiency by sequential acquisition. Speed advantages of the embodiments of FIG. 5 and FIG. 6 may be related to the absence of moving parts and minimization of overlap between imaging sensors.

Figure 7:
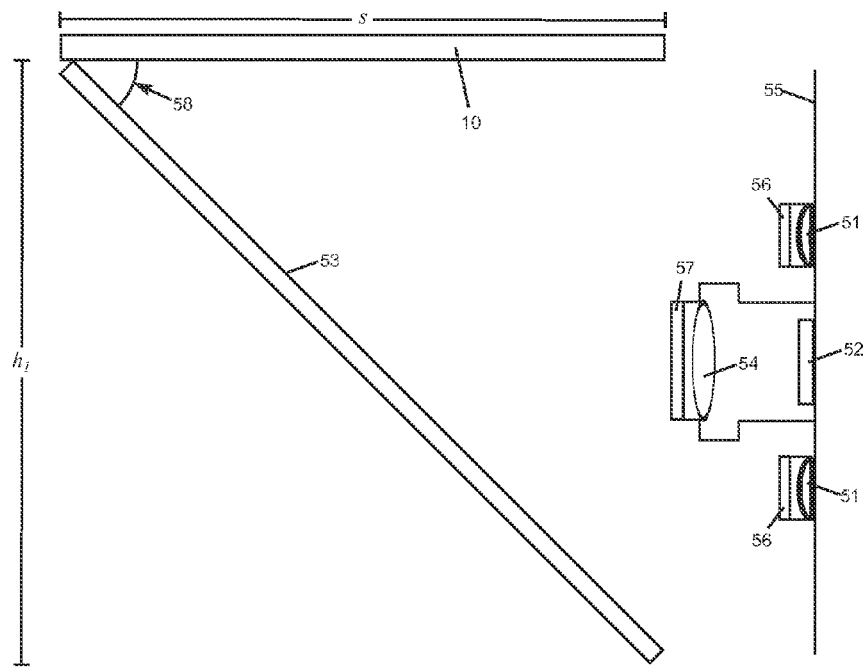
FIG. 7 is a diagram illustrating an image capture system comprising a stationary sensor, mirror, sensors, and polarizers of an embodiment of the present invention.

Additional embodiments of the present invention may also comprise stationary image capture systems, and may utilize fewer sensors than the embodiments of FIG. 5 and FIG. 6. FIG. 7 is a diagram illustrating an image capture system comprising a stationary sensor, mirror, sensors, and polarizers of an embodiment of the present invention. Sources 51 and a sensor 52 in this embodiment may be oriented in a non-parallel configuration relative to sheet 10. One or more mirrors, lenses, or other optical elements can direct light from sources 51 to sheet 10 and from sheet 10 to form an image on sensor 52. For example, light emitted from sources 51 can be reflected by a mirror 53 up to sheet 10. Light scattered by tissue in contact or above sheet 10 can be reflected again by mirror 53 toward sensor 52. Scattered light may also be focused onto sensor 52 with one or more lenses 54.

Sources 51 can be positioned in a variety of configurations. Sources 51 may, for example, be positioned in a shared plane 55 with sensor 52 or lens 54, or may be positioned in any other section of the device. Sources may be configured to be reflected by mirror 53 up to sheet 10 or to illuminate sheet 10 directly. In one embodiment of the present invention, sources 51 may be distributed in a ring or border around sensor 52 or lens 54. Alternatively, sources may be distributed in other areas of plane 55 not occupied by sensor 52. Multiple sensors and lenses may also be utilized, and in one embodiment can be distributed in plane 55 and optionally interleaved with sources 51. Lens 54 may be a wide angle lens or a non-distorting, e.g., non-wide angle lens, as the distance of sensor 52 from mirror 53 may not affect the stand-over height of the device in this embodiment.

In some embodiments of the present invention, polarizers 56 can be positioned in front of sources 51 as shown in FIG. 7. Polarizers 56 can be configured to polarize light emitted from sources 51 with any type of polarization, e.g., linear, circular, or elliptical polarization. Another polarizer 57 can be positioned in front of sensor 52. Polarizer 57 can be configured to shield sensor 52 from specular reflection, e.g., light emitted from sources 51 that is reflected by sheet 10 rather than scattered by tissue in contact or near sheet 10. For example, if polarizers 56 create clockwise circular polarization, polarizer 57 can be a counter-clockwise polarizer. Similarly, if polarizers 56 create linear polarization along a predetermined angle, polarizer 57 can be a linear polarizer of perpendicular orientation relative to said predetermined angle. These configurations can act as filters against light emitted from sources 51 that has not undergone a polarization change, e.g., through scattering by the foot being imaged.

Sources 51 and sensor 52 can be positioned at any side of sheet 10; dimension s may be the short or long dimension of sheet 10. In one embodiment of the present invention, sheet dimension s can be a short dimension of sheet 10, e.g., such that mirror 53 extends across a longer dimension of sheet 10. This embodiment may create a lower stand-over height for sheet 10 relative to a configuration where sheet dimension s is the longer dimension of sheet 10. In another embodiment of the present invention, multiple mirrors and sensors can be utilized, e.g., at least one mirror per foot.

Angle 58 in the embodiment of FIG. 7, e.g., an angle of mirror 53 from horizontal, may be between 44 degrees and 46 degrees, inclusive. However, angle 58 may also be less than 45 degrees, including without limitation between 30 degrees and 35 degrees, 35 degrees and 40 degrees, or 40 and 45 degrees, inclusive, or any integer or non-integer number of degrees within or between the enumerated ranges. Shared plane 55 can perpendicular to sheet 10. Alternatively, shared plane 55 can have some amount of tilt, e.g., be tailored to the degree of angle 58 for optimal image capture from mirror 53. For example, if angle 58 is less than 45 degrees, plane 55, e.g., sensor 52 and lens 54, may be tilted downward by some amount. Sensor 52 and lens 54 can be positioned at a vertical midpoint, e.g., $h_1/2$ below sheet 10, but may also be positioned above or below such midpoint. For example, in one embodiment, sensor 52 and lens 54 can be positioned less than $h_1/2$ below sheet 10.

Figure 8:
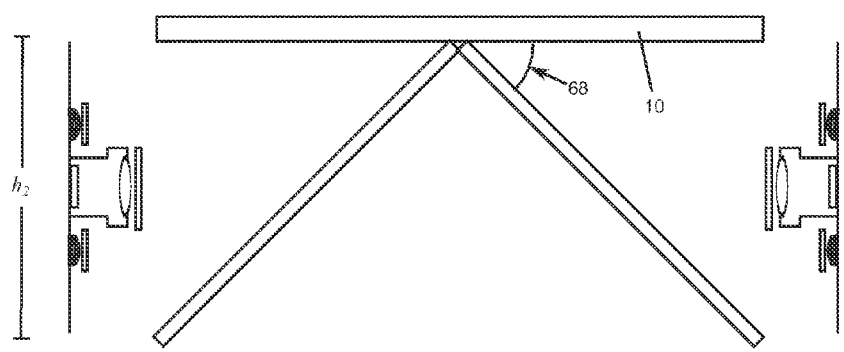
FIG. 8 is a diagram illustrating a periodic monitoring device comprising laterally positioned sources and sensors with angled mirrors bisecting the transmissive sheet.

In another embodiment of the present invention, two halves of sheet 10 can be imaged by separate sets of sources and sensors. FIG. 8 is a diagram illustrating a periodic monitoring device comprising laterally positioned sources and sensors with angled mirrors bisecting the transmissive sheet. Sheet 10 can be bisected along the direction that is intended to be parallel to a patient's two feet, e.g., between a patient's two feet such that each set of sources and sensors images a single foot. Sheet 10 may alternatively be bisected perpendicularly to this direction, and a final image of one or two of a patient's feet can be reconstructed by image stitching or other image data combination methods. Angle 68 in the embodiment of FIG. 8 may have any of the values enumerated with respect to angle 58 in the embodiment of FIG. 7. Sensors, lenses, and other elements in this embodiment can also be configured similarly to sensor 52, lens 54, and other such elements of FIG. 7. A particular advantage of the embodiment of FIG. 8 may be a shortened stand-over height relative to the embodiment of FIG. 7. For example, in FIG. 8 stand-over height $h_2$ may be significantly smaller than the stand-over height $h_1$ of the embodiment of FIG. 7.

Figure 9:
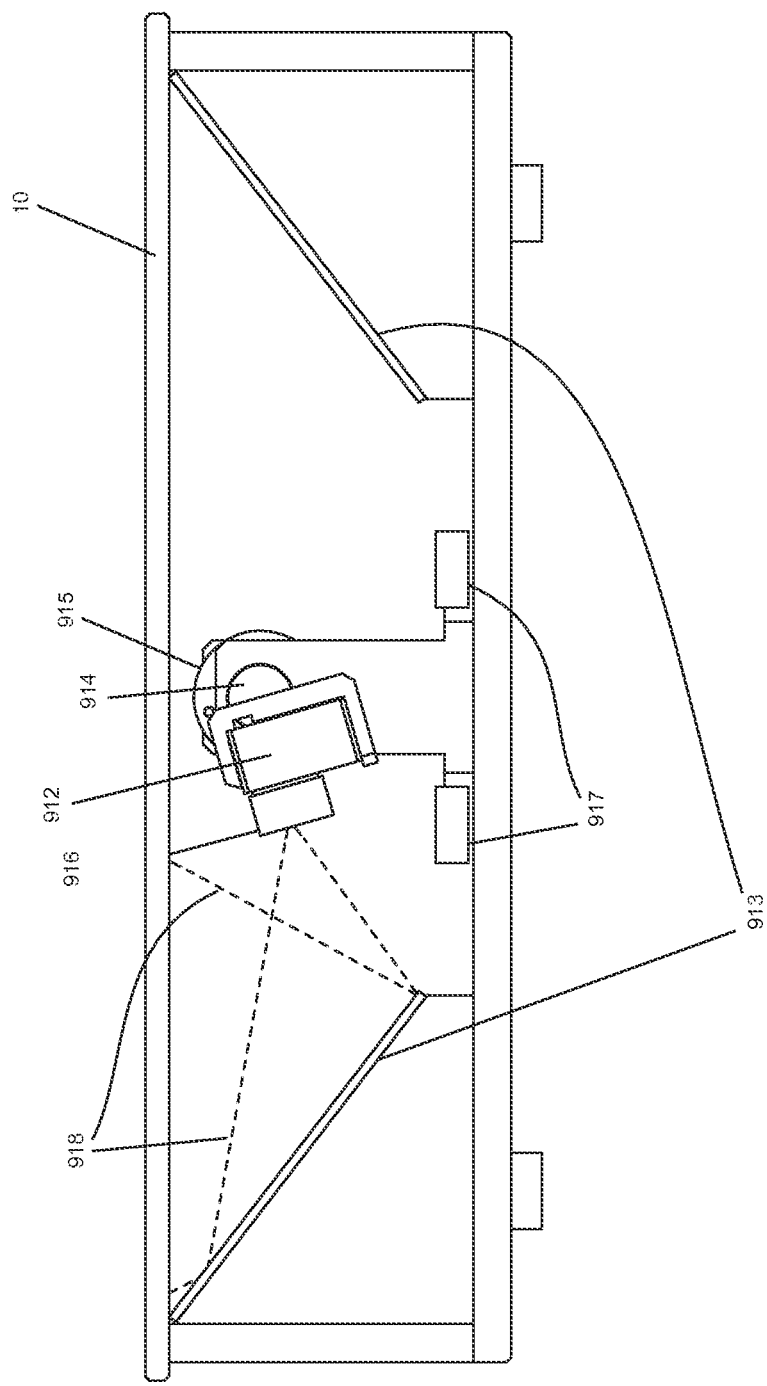
FIG. 9 is a diagram illustrating an additional embodiment of the present invention comprising angled mirrors and one or more cameras to create a low-profile imaging platform.

FIG. 9 is a diagram illustrating an additional embodiment of the present invention comprising angled mirrors and one or more cameras to create a low-profile imaging platform. In the embodiment of FIG. 9, a sensor 912 and lens 916 or a camera may be positioned at or near the center of sheet 10. Mirrors 913 may be positioned at an angle to direct light toward sensor 912. Two or more sensors may be utilized, e.g., at least one sensor directed at each of mirrors 913, or a single sensor may be utilized and rotated between each of mirrors 913. A sensor 912 may, for example, be mounted on a rotatable or movable element 914 controlled by a motor 915 configured to rotate between image acquisitions from mirrors 913. Motor 915 may be a servomotor, stepper motor, or any other type of electric motor in possible conjunction with additional actuating elements.

Illumination sources may be collocated with sensor 912, e.g., in the form of a camera unit or in similar configurations to those shown in the embodiments of FIG. 7 and FIG. 8, but may also be located anywhere else within the device in a manner to illuminate sheet 10. For example, illumination sources 917 can be positioned relatively lower than sensor 912 as shown in FIG. 9, or in another manner to illuminate sheet 10 directly. In this embodiment, sources 917 can comprise LED's, lamps, or other sources emitting white, single-color, infrared, or near-infrared light. Sources 917 may optionally include diffusive elements, including but not limited to casings or layers of plastic or semi-opaque materials, to increase uniformity of illumination.

In the embodiments of FIG. 9 and similar embodiments, the positioning of mirrors, sensors, and other elements may be configured to provide a clinically useful field of view, e.g., accommodating a patient's foot or feet, while minimizing the stand-over height of the device. Mirrors may be positioned at an angle relative to sheet 10, e.g., and angle below horizontal, less than or equal to 45 degrees. Mirrors may also be positioned at an angle relative to sheet 10 that is between 45 degrees and 42.5 degrees, 42.5 degrees and 40 degrees, 40 degrees and 37.5 degrees, 37.5 degrees and 35 degrees, or 35 degrees and 30 degrees, inclusive, or any other integer or non-integer number of degrees within or between the enumerated ranges. Mirrors can, for example, be positioned at 36.2 degrees, 37.5 degrees, 38.11 degrees, 40.9 degrees, 41.25 degrees, or any other integer or non-integer number of degrees less than or equal to 45 degrees.

Sensors can be configured in a variety of positions or orientations. In one embodiment of the present invention, sensor 912 and lens 916 can be vertically aligned with the midpoints of mirrors 913. In another embodiment of the present invention, sensor 912 and lens 916 can be positioned relatively higher than the midpoints of mirrors 913. Sensors and lenses can, for example, be positioned vertically between the midpoints, e.g., vertical midpoints, of mirrors 913 and sheet 10. Alternatively, sensors can be positioned between the midpoints of mirrors 913 and the bottom of the device. Sensor 912 and lens 916 can also be tilted, e.g., downward as shown in the embodiment of FIG. 9. Sensors can have a tilt, e.g., off vertical, between 0 and 45 degrees. Sensors can further have a tilt between 45 degrees and 42.5 degrees, 42.5 degrees and 40 degrees, 40 degrees and 37.5 degrees, 37.5 degrees and 35 degrees, or 35 degrees and 30 degrees, inclusive, or any other integer or non-integer number of degrees within or between the enumerated ranges. Tilt of a sensor or sensors in this embodiment can be related to the angles at which mirrors 913 are positioned. Tilt of a sensor or sensors can also be related to the vertical positioning of the sensor and the distance of the sensor from a mirror.

Dimensions of mirrors 913 may be tailored to achieve a predetermined field of view, and can be related to the configuration, e.g., angular orientation and positioning, of mirrors and sensors in this embodiment. Length of mirrors 913, e.g., the dimension of mirrors 913 extending into or out of the page in the view of FIG. 9, can be between 25 cm and 50 cm, 28 cm and 45 cm, 30 cm and 40 cm, or 33 cm and 38 cm, inclusive, or any integer or non-integer length within the enumerated ranges. For example, length of mirrors 913 may be 30.48 cm, 34.29 cm, 35 cm, 35.5 cm, 14.9 cm, and so forth. Width of mirrors 913, e.g., the dimension of mirrors 913 visible in the view of FIG. 9, can be between 7 cm and 18 cm, 8 cm and 15 cm, 9 cm and 14 cm, or 10 cm and 13 cm, inclusive, or any integer or non-integer length between the enumerated values. Width of mirrors 913 may, for example, be 11.7 cm, 12.5 cm, 13.22 cm, or 14.25 cm, inclusive, or any similar such width.

Configuration of mirrors and a sensor or sensors in the embodiment in the manners that have been described can allow a relatively short stand-over height to be implemented while maintaining a clinically useful field of view; exemplary outer ray paths 918 are shown in FIG. 9 and can enclose a relatively large area of sheet 10. The height of the image capture system in this embodiment can be less than or equal to 23 cm. The height of the image capture system in this embodiment can further be equal to or less than 18 cm, 14 cm, 13.5 cm, 13 cm, 12.5 cm, 12 cm, 11.5 cm, 11 cm, 10.5 cm, or 10 cm, inclusive, or any other integer or non-integer number of centimeters between the enumerated values.

Figure 10:
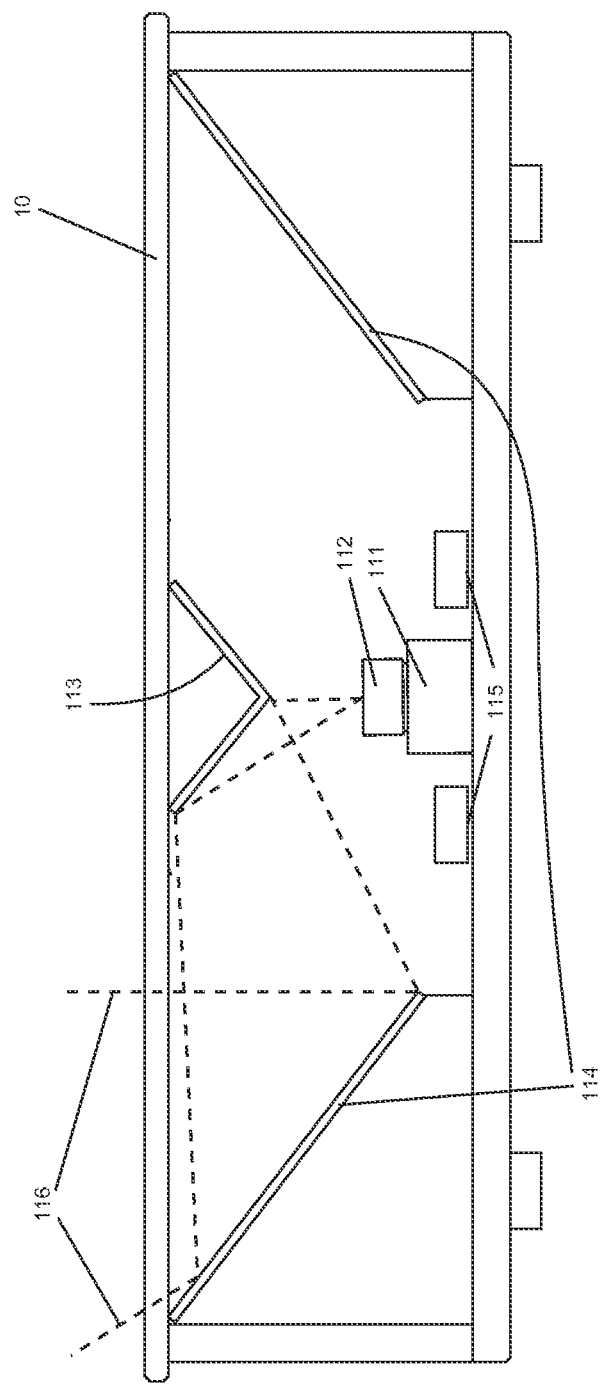
FIG. 10 is a diagram representing an imaging device comprising a plurality of reflective elements creating multi-step optical paths between a transmissive sheet and optical sensor of one embodiment of the present invention.

Embodiments of the present invention may also utilize mirrors or other reflective or optical elements to create multi-step optical paths between sheet 10 and an optical sensor. FIG. 10 is a diagram representing an imaging device comprising a plurality of reflective elements creating multi-step optical paths between a transmissive sheet and optical sensor of one embodiment of the present invention. The embodiment of FIG. 10 may contain no moving parts while obtaining images from two fields of view, e.g., of two feet, using a single sensor or camera. This embodiment may comprise a central sensor 111 and lens 112 positioned below central mirrors 113. Central mirrors 113 can, for example, be a single V-shaped mirror or reflective element or may be two angled mirrors positioned adjacent to one another to form a V-shape. Outer mirrors 114 can be positioned similarly to the embodiment of FIG. 9, in a manner to reflect an image from sheet 10 to one side of central mirrors 113. Central mirrors 113 can be configured to reflect and focus the image onto central sensor 111. In one embodiment of the present invention, central mirrors 113 and central lens 112 can be configured to focus the image from one of outer mirrors 114 onto half of sensor 111, and the image from the other of outer mirrors 114 onto the second half of sensor 111. In this embodiment, two fields of view, e.g., of two feet, can be simultaneously acquired as a single image on central sensor 111. Exemplary outer ray paths 116 are shown on one side of the drawing; similar ray paths may be expected between outer and inner mirrors in the other half of the device.

Sources 115 in the embodiment of FIG. 10 can be provided in any of the configurations that have been described. For example, sources 115 can be positioned as shown, below lens 112 and configured to diffusely illuminate sheet 10. Sources 115 can also be positioned, e.g., as illustrated in FIG. 10, in a manner such that specular reflection of sources 115 on sheet 10 is outside the field of view of sensor 111. Sources 115 can comprise LED's, lamps, or other sources emitting white, single-color, infrared, or near-infrared light. Sources 115 may optionally include diffusive elements, including but not limited to casings or layers of plastic or semi-opaque materials, to increase uniformity of illumination.

Outer mirrors 114 may be positioned at an angle relative to sheet 10, e.g., an angle below horizontal, less than or equal to 45 degrees. In some embodiments of the present invention, this angle can be as little as 8 degrees. Outer mirrors 114 may also be positioned at an angle relative to sheet 10 that is between 45 degrees and 42.5 degrees, 42.5 degrees and 40 degrees, 40 degrees and 37.5 degrees, 37.5 degrees and 35 degrees, or 35 degrees and 30 degrees, inclusive, or any other integer or non-integer number of degrees within or between the enumerated ranges. Outer mirrors can, for example, be positioned at 36.2 degrees, 37.5 degrees, 38.11 degrees, 40.9 degrees, 41.25 degrees, or any other integer or non-integer number of degrees less than or equal to 45 degrees.

Central mirrors 113 can be parallel to outer mirrors 114, e.g., such that the angle below horizontal of each of central mirrors 113 is equal to the corresponding angle of outer mirrors 114. Alternatively, the angles of central mirrors 113 may be slightly offset from the angles of outer mirrors 114. For example, angles of central mirrors 113 from horizontal may differ from those of outer mirrors 114 by between 0.1 degrees and 1 degree, 1 degree and 2 degrees, 2 degrees and 3 degrees, 3 degrees and 4 degrees, or 4 degrees and 5 degrees, inclusive, or any other integer or non-integer number of degrees within or between the enumerated ranges.

The length of outer mirrors 114, e.g., the dimension of outer mirrors 114 extending into or out of the page in the view of FIG. 10, can be between 25 cm and 50 cm, 28 cm and 45 cm, 30 cm and 40 cm, or 33 cm and 38 cm, inclusive, or any integer or non-integer length within the enumerated ranges. For example, length of outer mirrors 114 may be 30.48 cm, 34.29 cm, 35 cm, 35.5 cm, 14.9 cm, and so forth. Width of outer mirrors 114, e.g., the dimension of outer mirrors 114 visible in the view of FIG. 10, can be between 7 cm and 19 cm, 7.5 cm and 15 cm, 8 cm and 14 cm, or 9 cm and 12 cm, inclusive, or any integer or non-integer length between the enumerated values. Width of outer mirrors 114 may, for example, be 10 cm, 11.5 cm, 12.54 cm, or 13.11 cm, inclusive, or any similar such width.

The length of central mirrors 113, e.g., the dimension of central mirrors 113 extending into or out of the page in the view of FIG. 10, may be equal to length of outer mirrors 114. However, the length of inner mirrors 113 may be significantly less than length of outer mirrors 114, e.g., be 10%, 20%, 30%, 40% or 50% of the length of outer mirrors 114, or any integer or non-integer percentage of the length of outer mirrors 114 between the enumerated values. Width of central mirrors 113, e.g., the dimension of inner mirrors 113 visible in the view of FIG. 10, can be between 1 cm and 5 cm, inclusive. Width of central mirrors 113 can further be between 2 cm and 3 cm, 3 cm and 4 cm, or 4 cm and 5 cm, and any integer or non-integer number of centimeters within or between the enumerated ranges. Width of central mirrors 113 can, for example, be 3.05 cm, 2.9 cm, 3.86 cm, or 3.44 cm, or any similar such widths.

The embodiment of FIG. 10 may be configured such that each field of view, e.g., the field of view reflected by each of outer mirrors 114, has a narrow dimension of at least 10 cm. This embodiment may further be configured such that each field of view has a narrow dimension of at least 11 cm, 12 cm, 13 cm, 14 cm, 15 cm, 16 cm, or 17 cm, inclusive, and any integer or non-integer number of centimeters between or above the enumerated values. The embodiment of FIG. 10 may also be configured such that each field of view has a long dimension of at least 24 cm. This embodiment may further be configured such that each field of view has a long dimension of at least 28 cm, 29 cm, 30 cm, 31 cm, 32 cm, 33 cm, or 34 cm, inclusive, and any integer or non-integer number of centimeters between or above the enumerated values. Each of these fields of view can occupy a discrete area of a continuous sheet 10. However, in this embodiment sheet 10 may also be sectioned into multiple pieces, e.g., one piece for each field of view where a space dividing the pieces may or may not be transmissive.

Distance between two discrete fields of view, e.g., such as those described with respect to the embodiments of FIG. 9 or FIG. 10, can be between 10 cm and 100 cm, inclusive. This distance may also be between 10 cm and 50 cm, 15 cm and 40 cm, or 20 cm and 30 cm, inclusive, or any integer or non-integer number of centimeters within the enumerated ranges. These or other amounts of space between two fields of view can increase comfort of use of the device in these embodiments of the present invention as diabetic and other patients may prefer relatively wide stances. Space between the fields of view may therefore accommodate a more natural patient stance during use while allowing image capture hardware to be located within a clean, minimized overall device footprint area.

In one embodiment of the present invention, the optical distance between central mirrors 113, lens 112, and sensor 111 can be secured. Central mirrors 113, lens 112, and sensor 111 can, for example, be secured to a shared vertical support or supports. Such a shared vertical support can be outside of the field of view of sensor 111, e.g., can be secured to sides of central mirrors 113, lens 112, and sensor 111 that are not in any ray paths between outer mirrors 114 and inner mirrors 113. In the view of FIG. 10, this positioning could be in front of or behind mirrors 113, e.g., as opposed to on the right or left of mirrors 113. Vertical supports can be plastic, wood, metal, or any other supporting material or combination thereof. Central mirrors 113, lens 112, and sensor 111 can further be incorporated into an integrated unit, or otherwise secured relative to one another.

Embodiments of the present invention, including but not limited to those embodiments described with respect to FIG. 9 and FIG. 10, can be configured for operation with sensor or camera lenses having diagonal fields of view between 50 degrees and 90 degrees, inclusive, or any other integer or non-integer number of degrees within the enumerated range. Embodiments can, for example, be configured for operation with a lens having a diagonal field of view of 84.1 degrees, 75.4 degrees, or 63.4 degrees, or any similar such angle. Embodiments of the present invention can also be configured for sensors having aspect ratios or aspect ratio options of 4:3, 3:2, 16:9, 5:3, 5:4, 1:1, or any other aspect ratios. In the embodiment of FIG. 10, central sensor 111 can be positioned such that a wider aspect accommodates two fields of view, e.g., such that the wider aspect is split between images from each other mirrors 114, while the narrower aspect accommodates the length of each foot during imaging. Alternatively, central sensor 111 can be positioned 90 degrees from this orientation, e.g., with a wider aspect aligned with the length of a foot during imaging.

Embodiments of the present invention can also comprise internal-reflection based image capture systems. In these embodiments, sensors can be positioned and configured with respect to sheet 10 in any of the manners that have been described. Source positioning may be tailored for total internal reflection-based imaging. Total internal reflection can occur where a beam of light meeting an interface between two transparent or semi-transparent, e.g., non-scattering or absorbing, materials undergoes an amount of refraction sufficient to redirect the beam along the interface or back into the first material rather than passing into the second. The angular change in the beam's path due to refraction at such interfaces can be described by Snell's law, $n_1 \sin \varphi_1 = n_2 \sin \varphi_2$ with $n_1$ and $n_2$ being the refractive indices of the materials on the first side of the interface and second side of the interface, respectively, and $\varphi_1$ and $\varphi_2$ being its incoming and outgoing angles of incidence, respectively. Rearranging Snell's law for incident angles resulting in $\varphi_2$ being 90 degrees or more yields that an incident angle $\varphi_1 = \sin^{-1} n_2/n_1$ can result in total internal reflection.

Figure 11:
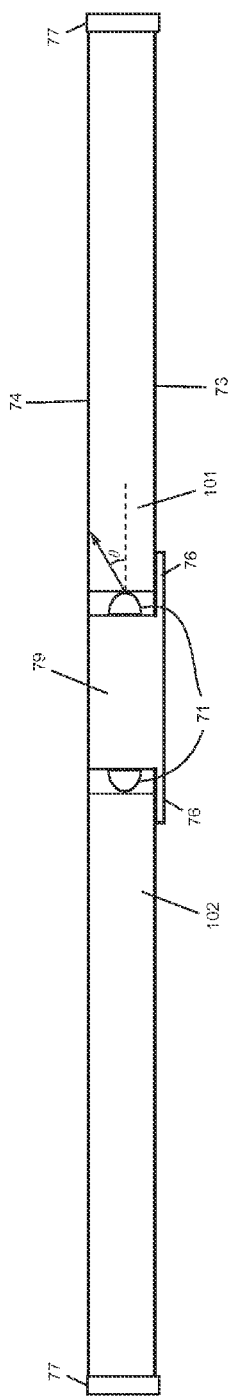
FIG. 11 is a diagram illustrating a source configuration for an internal reflection-based image capture system of an embodiment of the present invention.

FIG. 11 is a diagram illustrating a source configuration for an internal reflection-based image capture system of an embodiment of the present invention. This embodiment may comprise one or more sources 71 positioned along edges of a transmissive sheet. Sources 71 may be positioned along an outer edge or edges of a transmissive sheet, e.g., sheet 10, but as shown in the embodiment of FIG. 11 can be positioned along inner edges of a segmented sheet. In this embodiment, the transmissive sheet comprises a right segment 101 and a left segment 102. Light emitted by source 71 at angles less than a predetermined angle θ relative to the sheet can be totally internally reflected, in the absence of contact with external materials. As discussed later with respect to image analysis, information regarding the amount and locations of tissue in contact with the sheet may help identify regions which experience pressure while the patient is standing in a neutral position and track changes in loading that could lead to ulcer formation.

In embodiments of the present invention, total internal reflection can occur at the upper interface 73 and lower interface 74 of sheet segment 101 or 102. When an external material, such as the tissue of a patient's foot, comes into contact with upper interface 74, it can scatter light incident on the interface at that point and change the angle of incidence at which the light leaves interface 74. This altered angle of incidence can be steeper than the limit for total internal reflection and may therefore escape segment 101 through lower interface 73. A sensor or array of sensors 75, e.g., similar to the sensor and lens array of the embodiment of FIGS. 3 and 4, may be arranged in a plane below lower interface 73. Responses of sensors 75 can be utilized to reconstruct an image of tissue in contact with segment 101.

A maximum angle θ of light emission from source 71 resulting in total internal reflection may be determined by $$\theta = \left(90° - \sin^{-1}\frac{n_2}{n_1}\right),$$

where $n_1$ is the index of refraction of the sheet and $n_2$ is the index of refraction of surrounding air. In embodiments of the present invention wherein air is on both sides of sheet 10, $n_2$ may be equal to 1.00. The index $n_1$ for the material of the sheet may be predetermined, or may be determined by one of a variety of methods including but not limited to Emmons double variation, automated or manual temperature variation, dispersion staining, or other immersion methods. Sheets may have an index of refraction between 1.00 and 2.00, but may also have a greater index of refraction. Sheets may further have an index of refraction between 1.2 and 1.8, 1.3 and 1.7, or 1.4 and 1.6, inclusive, and any index within the enumerated ranges. Indices of refraction can be specific to different wavelengths of light. Indices of refraction corresponding to the wavelength or wavelengths emitted by source 71 can be utilized for calculation purposes. Alternatively, angle θ may be determined by device calibration or pre-assembly testing, such as by measuring light outside of a sheet, varying the angle of source 71 in small increments, and selecting angle θ where light outside the sheet is minimized or zeroed.

To minimize light escaping segment 101 or segment 102 during imaging, e.g., through lower interface 73 and saturating sensors below the sheet, sources 71 may be collimated to angle θ. Alternatively, light emitted by source 71 at angles greater than angle θ can be absorbed in a region of absorbers 76 positioned below the sheet. The length of region of absorbers 76 may be at t/2 tan θ where t is the sheet thickness.

Angle θ may be between 0 and 90 degrees. Angle θ may further be between 10 and 70 degrees, 20 and 60 degrees, or 30 and 50 degrees, inclusive, or any other integer or non-integer number of degrees within the enumerated ranges. Length of absorbers 76 can be between 0.5 cm and 2.54 cm, 0.8 cm and 2.3 cm, or 1 cm and 1.78 cm, inclusive, or any other length within the enumerated ranges. Absorbers 76 can be any material absorbent of light with wavelengths emitted by source 71. These materials may include but are not limited to black or darkly colored plastics, wood, non-reflective paint, or other pigmented or non-reflective materials. Housing 79 between segments 101 and 102 may be the same material as absorbers 76 or any other opaque or non-opaque material.

Source 71 in the present embodiment may be one or more light-emitting diodes (LED's), lasers, cold cathode fluorescent lamps (CCFL), xenon lamps, other lamps, or any other optical sources. A source or sources may for example be a row of LED's across an edge of the sheet or a lamp extending across the edge. Alternatively, a source or sources may be positioned on either side of the edge with a reflective element configured to distribute emitted light across the edge. Any edge or edges of sheet 10 may be lined with a mirror 77 or other reflective element or coating. Mirrors 77 can reflect light not scattered during one transit across segment 101 or 102. Mirrors 77 can be tailored to fully cover an edge the sheet, e.g., to be at least as tall as the sheet thickness and at least as long as the respective edge. Mirrors 77 utilized in the embodiment of FIG. 11 and other embodiments having sources configured for TIR illumination can improve the uniformity and efficiency of illumination and imaging.

Figure 12:
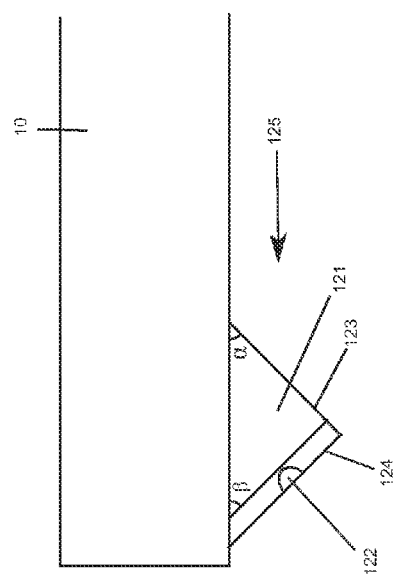
FIG. 12 is a diagram representing another TIR source configuration of an embodiment of the present invention.

FIG. 12 is a diagram representing another TIR source configuration of an embodiment of the present invention. A surface-mounted total internal reflection source configuration 125 of this embodiment can comprise a prism 121 attached to the underside of sheet 10. Prism 121 may be attached to sheet 10 by a transparent or semi-transparent adhesive or epoxy. The adhesive may have an index of refraction matched to the index of prism 121, sheet 10, or a shared index of the two. Alternatively, prism 121 may be secured to sheet 10 by another fastening mechanism, including but not limited to side arms or supports, or other metal, plastic, components that are opaque or, if transparent, index-matched to prism 121 and sheet 10.

A light source 122 can be directed into one side of prism 121, which can transmit said light into sheet 10. Prism 121 and light source 122 may be configured such that emitted light that is transmitted into sheet 10 is transmitted at an angle resulting in total internal reflection. Light may also be emitted at angles that escape through the top surface of sheet 10. Light escaping through the top surface of sheet 10 may not interfere with images being acquired, e.g., by saturating a camera or sensor positioned below sheet 10, in the manner that light escaping through the bottom surface of sheet 10 may. Light source 122 can be adhered directly to prism 121 or may be provided on a backing 124. Backing 124 can include without limitation foils, e.g., copper foil, or any board or backing. Backing 124 may provide electrical connectivity to control and provide power to source 122 and may also serve as a heat sink for thermal management of source 122. Source 122 may comprise any one or combination of LED's, LED chips, incandescent bulbs, flash bulbs, or lamps, with or without additional optical components such as lenses.

Another side of prism 121 may be coated with a reflective material, lined with a mirror, or otherwise configured to be a reflective surface 123. Reflective surface 123 can further prevent light emitted from source 122 from polluting acquired images. However, in another embodiment of the present invention, a second source can be provided, and positioned facing into prism 121, e.g., en lieu of reflective surface 123.

In one embodiment of the present invention, prism 121 can have two equal angles at the interface with sheet 10; angle α and angle β of FIG. 12 can be equal angles. For example, angle α and angle β may both equal 45 degrees. In other embodiments of the present invention, angle α can be less than angle β. In such embodiments, angle α may be between 1 degree and 44 degrees, inclusive. Angle α may further be between 10 degrees and 40 degrees, 15 degrees and 38 degrees, 20 degrees and 36 degrees, or 25 degrees and 35 degrees, inclusive, or any other number of integer or non-integer degrees within the enumerated ranges. Angle β may be equal to the difference between 90 degrees and angle α. Relatively smaller angles of angle α may provide particularly uniform TIR illumination.

In one embodiment of the present invention, prism 121 may be configured such that angle α is as small as possible, e.g., given the size of source 122 and backing 124. The size of source 122 and backing 124 can be minimized in a variety of ways, including but not limited to use of LED or LED chip sources smaller than 5 mm in diameter. LED chips can further be less than 4 mm, 3 mm, 2 mm, or 1 mm in diameter. Precise timing synchronization between source 122 and a sensor during image capture can also reduce the thermal management requirements for backing 124 as this can allow source 122 to be illuminated for a relatively short period of time. Timing synchronization can be enabled by one of a variety of methods, including but not limited to a flash sync signal or other wired or wireless signal between a sensor and source 122.

Each free side of prism 121, e.g., a side opposite angle α or angle β, may be between 0.1 cm and 5 cm, inclusive, or any other integer or non-integer number of centimeters within the enumerated range. Each free side of prism 121 may further be between 0.3 cm and 1 cm, e.g., such as when a relatively small source 122 is utilized. Sides may also be between 0.5 cm and 1 cm, 1 cm and 3 cm, or 3 cm and 4 cm, inclusive.

Embodiments of the present invention comprising the TIR source configuration illustrated in FIG. 12, e.g., a source mounted below sheet 10 configured for TIR, may be particularly compact or may facilitate hygienic maintenance of the device, e.g., as compared to side-mounted TIR source configurations. This configuration may allow the device to be housed in a box-like manner with few to no complex features around edges of the housing, such as the housing configuration illustrated in FIG. 3. Such self-contained configurations can allow the device to be more easily cleaned, and may also increase the portability and robustness of a device.

Figure 13:
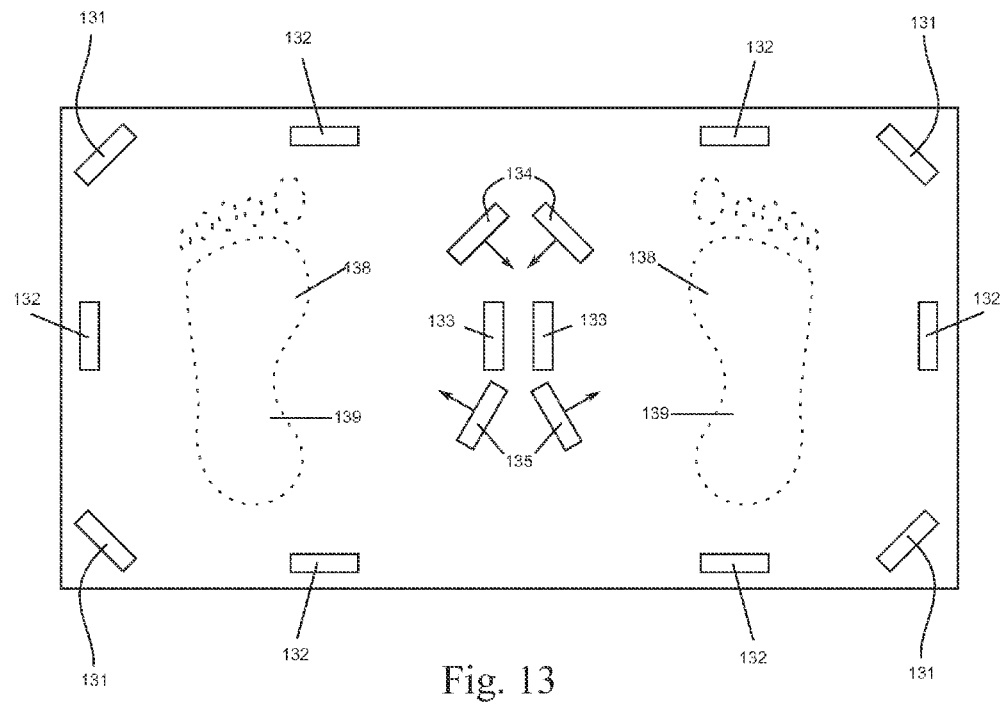
FIG. 13 is a diagram showing a number of possible locations of source-prism combinations on a transmissive sheet.

In embodiments of the present invention, a source-prism combination as shown in FIG. 12 can be positioned anywhere on the area of sheet 10. However, positions on sheet 10 may be selected that are not imaged by the image capture system, or that do not interfere with a view of tissue in contact with sheet 10 during use of the system. Multiple source-prism combinations can be utilized. For example, two, three, four, or more source-prism combinations can be positioned on the underside of sheet 10. FIG. 13 is a diagram showing a number of possible locations of source-prism combinations on sheet 10. Source-prism combinations can be positioned at all of these positions, a subset of these positions, or different positions. Source-prism combinations can, for example, be positioned at 1, 2, 3, or 4 of the corner positions 131 shown on the rectangular sheet 10 shown in FIG. 13. Source-prism combinations can also or alternatively be positioned at 1, 2, 3, 4, 5, 6, or more lateral positions 132, as shown or similar to those shown in FIG. 13. Source-prism combinations can also or alternatively be positioned at 1, 2 or more central positions 133. Source-prism combinations may also extend across the length of one or more sides of sheet 10 or along one or more central axes of sheet 10.

In some embodiments of the present invention, source-prism combinations can be configured to enhance TIR image quality of particular regions of a foot during device use. For example, positioning of source-prism combinations can be configured to enhance image quality of metatarsal region 138, instep region 139, or additional regions of the foot. Image quality in regions that are first struck by TIR light can be higher than those regions that are subsequently illuminated, as the intensity of light within the glass can decrease once scattering occurs. For example, as illustrated in FIG. 13 upper angled sources 134 may preferentially illuminate instep region 139. Similarly, lower angled sources 135 may preferentially illuminate metatarsal region 138. Upper angled sources 134 and lower angled sources 135 may be positioned between 20 degrees and 50 degrees from vertical. These sources may further be positioned between 25 degrees and 30 degrees, 30 degrees and 35 degrees, 35 degrees and 40 degrees, or 40 degrees and 45 degrees, inclusive, or any integer or non-integer number of degrees within the enumerated ranges. Upper angled sources 134 may be positioned at least 1 cm away, e.g., vertically from an upper edge of sheet 10, e.g., and edge toward which it is intended for toes to point during use. Upper angled sources may also be positioned at least 2 cm, 3 cm, 4 cm, 5 cm, or 6 cm away from this upper edge, or any integer or non-integer number of centimeters between or above the enumerated values. Lower angled sources 135 may be positioned at least 10 cm away from said upper edge. Lower angled sources may further be positioned at least 12 cm, 14 cm, 16 cm, 18 cm, 20 cm, 22 cm, or 24 cm away from said upper edge of sheet 10, inclusive, and any other integer or non-integer number of centimeters between or above the enumerated values.

Excessive moisture, e.g., from a patient's foot or other sources such as condensation, on upper interface 74 or lower interface 73 can degrade image quality or accuracy. Moisture or liquid on sheet 10 can be particularly detrimental for internal reflection-based image capture systems as the presence of water or liquids on interface 73 or 74 can disturb the condition for total internal reflection. In one embodiment of the present invention, moisture on sheet 10 can be managed by an air flow system configured to generate a flow of air across sheet 10. An air flow system may comprise a fan, intake, vent, or similar features. The air flow system may be configured to create a laminar flow of air, and may also optionally include a heater to control the temperature of air flowing across sheet 10. Heating air prior to fanning or blowing it across sheet 10 can increase the rate of vaporization of moisture or condensation on sheet 10.

In another embodiment of the present invention, an internal reflection-based image capture system can account for dirt, streaks, or similar imperfections on sheet 10. In this embodiment, a blank image, e.g., an image acquired without a patient standing on sheet 10, can be utilized. The blank image can be acquired immediately before or after acquiring images of a patient's feet. Features appearing in the blank image can be subtracted from images of a patient's feet. This embodiment can improve image accuracy and may avoid the occurrence of false alerts from dirt or streaks appearing as wounds or physical changes to a patient's foot.

In embodiments of the present invention, optical sensors and data connectivity between said sensors and outside networks can be provided. However, embodiments may alternatively be configured to couple with external devices having an optical sensor, including but not limited to mobile phones, personal tablet computers, digital cameras, and similar devices. For example, these embodiments may have a port or ports configured for insertion of an external device that aligns a sensor of the device appropriately for image capture. A port or ports can be tailored to a specific device, e.g., a specific mobile phone shape or model, or may be configured to be adjustable for accommodation of a range of devices. These embodiments may utilize the processing capabilities, wireless or cellular connections, or other functionalities of the external device.

Figure 14:
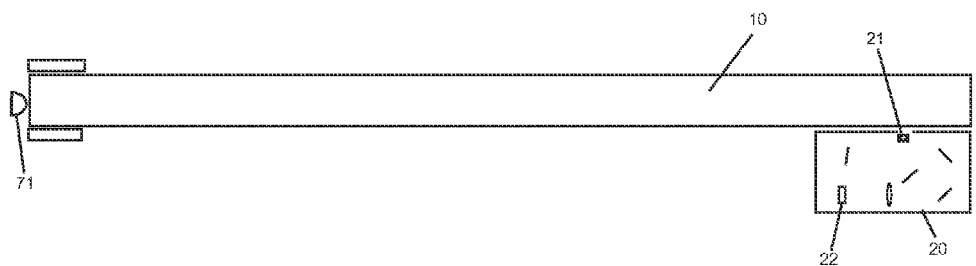
FIG. 14 is a diagram illustrating a monitoring device comprising a scanning image sensor and sources configured for multiple types of imaging of one embodiment of the present invention.

As previously described, e.g., with respect to FIG. 2, embodiments of the present invention can comprise multiple image capture systems, which may share hardware components or have independent components. FIG. 14 is a diagram illustrating a monitoring device comprising a scanning image sensor and sources configured for multiple types of imaging of one embodiment of the present invention.

A first image capture system can comprise a scanning image capture system and a second image capture system can comprise an internal reflection-based image capture system. A scanning element 20 can be configured with one or more sources and one or more sensors, e.g., as described for the embodiment of FIG. 4. A source 71 can be positioned adjacently to sheet 10, e.g., as described for the embodiments of FIG. 11.

In the embodiment shown in FIG. 14, a scanning image capture system and internal reflection-based image capture system can share a sensor or sensors. A shared sensor or sensors can be located on scanning element 20. During internal reflection-based imaging, source 71 can illuminate sheet 10 while scanning element 20 carries sensor 22 across sheet 10. During scanning imaging, a broadband source or single-color source on scanning element 20 can illuminate sheet 10 during the scan while sensor 22 collects photons scattered back down to scanning element 20 as previously described.

Alternatively, an internal reflection-based image system can utilize a sensor array positioned beneath sheet 10 and scanning element 20. In this embodiment, housing and mechanical actuators controlling scanning element 20 may be configured to allow scanning element 20 to be moved completely out of the area subtended by sheet 10 during internal reflection-based imaging to avoid obstruction of or interference with light from source 71 being reflected down to a source array.

Figure 15:
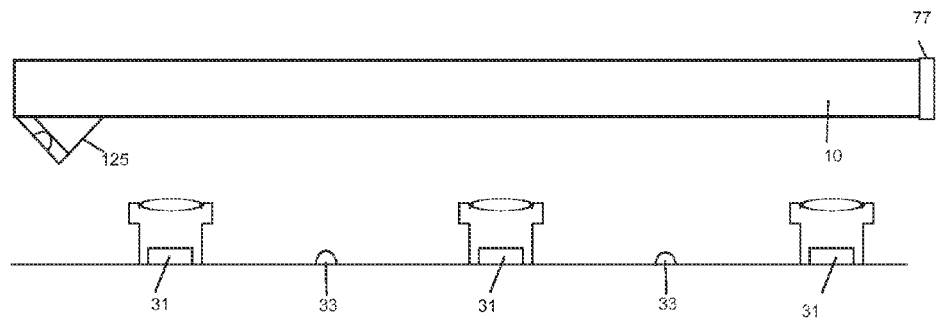
FIG. 15 is a diagram illustrating a monitoring device comprising a static sensor array and sources configured for multiple types of imaging of one embodiment of the present invention.

FIG. 15 is a diagram illustrating a monitoring device comprising a static sensor array and sources configured for multiple types of imaging of one embodiment of the present invention. A first image capture system can comprise an internal reflection-based image capture system and a second image capture system can comprise an array of sensors and lenses, e.g., as shown in the embodiments of FIG. 5 and FIG. 6. Sensor 52, lens 54, and mirror 53 can collect light from both internal reflection source configuration 125 and diffuse sources 33. Internal reflection source configuration 125 and diffuse sources 33 can illuminate sheet 10 sequentially, in any order.

Figure 16:
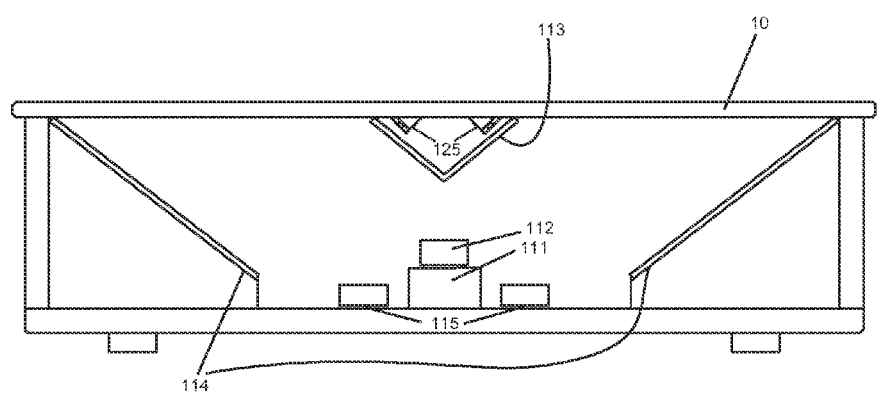
FIG. 16 is a diagram representing a monitoring device comprising a plurality of reflective elements creating multi-step optical paths between a transmissive sheet and optical sensor configured for multiple types of imaging of one embodiment of the present invention.

FIG. 16 is a diagram representing a multi-modality periodic monitoring device of the present invention comprising multi-step optical paths between a transmissive sheet and optical sensor configured for multiple types of imaging. As in the embodiment of FIG. 10, outer mirrors 114, inner mirrors 113, and lens 112 can focus multiple fields of view onto a central sensor 111, sensor array, or camera. In the embodiment of FIG. 16, multiple source types or locations can be provided to enable multiple image types to be acquired on sensor 111. For example, sources 115 can illuminate sheet 10 diffusely from below, e.g., as described with respect to the embodiments of FIG. 9 or FIG. 10, and a surface-mounted total internal reflection source configuration 125 can also be provided. The total internal reflection source can be surface-mounted, e.g., as described with respect to FIG. 12 and FIG. 13 and as shown in FIG. 16, or may be side-mounted, e.g., as described with respect to FIG. 11. Surface-mounted TIR source configuration 125 can be positioned anywhere on the surface of sheet 10, but in one embodiment can be positioned out of the field of view of sensor 111, such as by positioning relatively closer to a central axis of sheet 10 than the width of inner mirrors 113. The configuration shown in FIG. 16 can, for example, represent prism positioning related to central positions 133 or to central angled positions 134 or 135 of FIG. 13. Lower sources 114 and TIR source configuration 125 can emit white light, single-colored light, infrared light, near-infrared light, or any other type of light for imaging tissue in contact with or near sheet 10.

Figure 17:
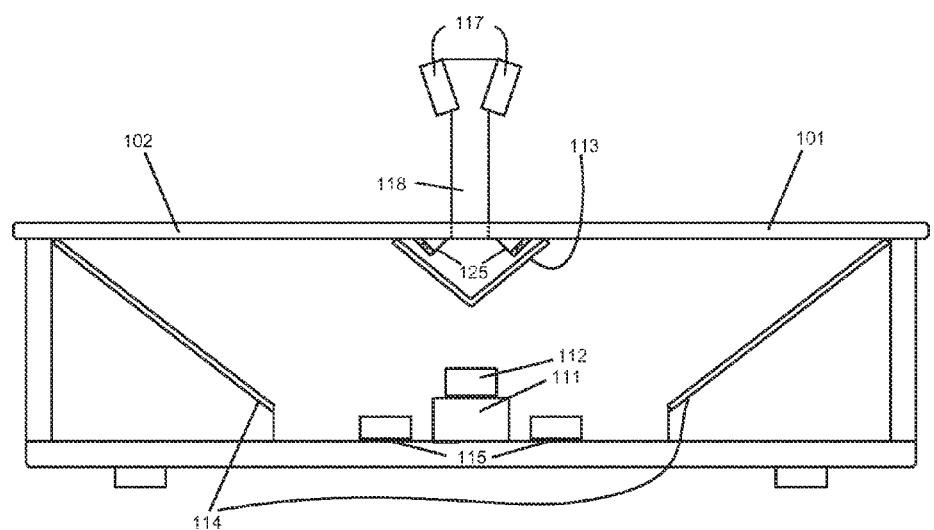
FIG. 17 is a diagram representing an embodiment of the present invention comprising a camera unit above the transmissive sheet.

In a further embodiment of the present invention, a camera or cameras can be mounted on or above sheet 10 and may be configured to acquire images of the top, sides, or backs of a patient's feet. FIG. 17 is a diagram representing an embodiment of the present invention comprising a camera unit above the transmissive sheet. A camera unit 118 can be configured with one or more lenses 117 configured to view the feet of a patient standing on the device from the side or from above. Camera unit 118 may be provided in conjunction with any of the additional image capture systems that have been described. In FIG. 17, camera unit 118 is shown above those image capture systems described with respect to the embodiment of FIG. 16. In this embodiment, camera unit 118 may be mounted on top of sheet 10. However, it may also be beneficial to section transmissive sheet 10 in two or more pieces, e.g., a right piece 101 and a left piece 102, with camera unit 118 mounted on an alternative surface between the two sheets. This can prevent camera unit 118 or any associated attachments or adhesives from scattering TIR light. While camera unit 118 can be positioned out of the field of view of sensor 111, scattering of TIR light may reduce the intensity of TIR light available for imaging regions of a patient foot on the transmissive sheet.

Camera units may be positioned near the center of a device, as shown in FIG. 17, but may also or alternatively be positioned above other regions of the sheet, including but not limited to the outer edges, front or back edges, corners, or any other regions. Camera units such as camera unit 118 can have any height, and lenses 117 can be positioned vertically or with any amount of tilt. For example, in one embodiment of the present invention, camera unit 118 can be configured with lenses 117 positioned between 2 cm and 20 cm above a transmissive sheet, inclusive, or any other integer or non-integer number of centimeters within the enumerated range. Lenses 117, e.g., and corresponding sensors within unit 118, may be positioned with a tilt up to 80 degrees from vertical. Lenses 117 can, for example, be positioned with no tilt, or with between 1 degree and 10 degrees, 10 degrees and 20 degrees, 20 degrees and 40 degrees, or 40 degrees and 50 degrees tilt, inclusive, or any other integer or non-integer number of degrees of tilt within the enumerated ranges.

Images acquired by an upper camera unit 118 and those images acquired by additional image capture systems within a shared device may be analyzed independently, e.g., to monitor all regions on the patient's feet, or in conjunction, such as to reconstruct three-dimensional images of the patient's feet. In another embodiment, a light-based, e.g., visible, near-infrared, or infrared-based, distance-sensing technology, for one example the apparatus described in U.S. Pat. No. 8,050,461 entitled "Depth-varying light fields for three-dimensional sensing," hereby incorporated by reference in its entirety, can be utilized to generate three-dimensional images from the sides, top, bottom, or back of the foot. Three-dimensional images may be useful for monitoring the presence of swelling, e.g., edema, or other three-dimensional changes in the patient's feet and may also be utilized for construction of custom insoles or patient footwear.

The multi-modality embodiments that have been described are in no way exclusive of other combinations or extensions of the imaging configurations of embodiments of the present invention. Any of the source types, positions, and configurations can be provided with any of the sensor or optical configurations that have been described to provide a low-profile, multi-modality foot imaging system.

In any of the embodiments of the present invention that have been described, image or data analysis can be performed, e.g., before, concurrently, or after image reconstruction, within a periodic monitoring device, such as in a logic chip, microcontroller, microprocessor, integrated circuit, or similar processing unit; in an external device such as a personal computer, smart phone, tablet, or handheld or other electronic device; or through a wireless network or similar connection, such as by cloud computing or other web or internet servers. Image or data analysis can include, without limitation, determination or approximation of the overall health of a foot, identification of injuries or at-risk sites of foot tissue, tracking and comparison of foot or tissue features or other tissue health parameters over time, or other interpretations of image data features, trends, or patterns.

Tissue color can also be analyzed in embodiments of the present invention. Specific colors or shades may be flagged as potentially at-risk sites. The amount, shape, or other parameters of a region of said color or shade can also be measured and may be included in the determination of a potentially at-risk site. For example, a region with pronounced tissue redness, e.g., exceeding a predetermined redness intensity threshold, may be flagged as a potentially at-risk site. The amount by which the tissue redness exceeds the threshold, the shape of region, size of region, and similar factors may be utilized to further predict the type of risk, e.g., if the region is a site of swelling, superficial irritation, wound, or, particularly, nonblanchable erythema. Nonblanchable erythema, e.g., tissue redness which does not reduce upon pressure application, can indicate a reversible, early-stage pressure ulcer. Since pressure can be applied to the sole of a patient's foot, e.g., pressure from the patient's weight, during imaging in embodiments of the present invention, nonblanchable erythema on the toes, metatarsals, heel, and other tissue in contact with the transmissive sheet may be visible in acquired images.

Similarly, calluses may be identified and flagged by whiteness or yellowness thresholds. Calluses may be classified as at-risk sites on the sole of a foot, as neuropathic patients may not feel or react to callus-related injuries, such as deep cracks in the callus requiring medical attention to avoid infection.

Identification of pronounced changes in color from past image data may be another mechanism for identification of at-risk or injured sites. For example, a patient may have foot health verified by a medical practitioner immediately prior to a preliminary image capture by a periodic monitoring device of the present invention. Color features and other aspects of this image can be used for reference values against which subsequent image data can be compared. Overall changes in the color pattern or color values on a patient's foot may also be flagged as indicators of changes in pressure-loading, tissue perfusion, or other conditions related to potential or existing injury or ulceration.

Analysis in embodiments of the present invention may also comprise identification or tracking of geometrical features in sole images, for example, contours representing contact with the transmissive sheet; total foot area in contact with the sheet; relative positioning of the toes, metatarsals, heel, or other regions of the foot; and so forth. These features may also be utilized as indicators of changes in pressure-loading, tissue perfusion, or other conditions related to potential or existing injury or ulceration. For example, a change in total tissue area in contact with the transmissive sheet may indicate that the pressure load experienced by contacting tissue has increased, as pressure is determined by force, e.g., a patient's weight, distributed over area, e.g., portions of the patient's foot contacting the ground or shoe bed when standing or walking. Detected changes in the aforementioned features, independent of further analysis, may be valuable in initiating a patient visit to a podiatrist or medical practitioner as tailored footwear, e.g., custom orthotics, physical therapy, or other means may be utilized to correct or adjust pressure loading to the patient's feet in light of physical changes.

Diabetic patients and other patients may have developed or be in the process of developing a number of physical changes in their feet, including but not limited to bunions, hammer toes, clawed toes, and Charcot Joint. Potentially damaged or at-risk sites on a patient's foot may be related to increased pressure application at or around one of these physical changes. Image processing or analysis in an embodiment of the present invention may optionally include detection for one or more of these types of physical conditions as well as features indicative of injury or ulceration. Detection in this embodiment may include analytical methods including Hausdorff distance calculation, edge detection, corner detection, blob detection, image convolution or cross-correlation, or other feature detection algorithms. Alternatively, detection may be implemented through machine learning methods, including but not limited to supervised learning algorithms or semi-supervised learning algorithms.

In one embodiment of the present invention, reconstructed images, with or without highlighting or indication of injured or prone regions identified by one of the aforementioned detection methods, may be displayed in a video format, e.g., as a temporal sequence of images. The sequence may comprise images representing daily, weekly, or monthly changes. This display format may be particularly useful for tracking the progression of an injury or change in a patient's foot, e.g., provide a visualization of color changes, spread, or other changes for analysis by the patient or medical practitioner.

One embodiment of the present invention may further comprise a patient verification or identification mechanism. A patient verification mechanism may comprise matching an acquired image to a reference image or set of previous images taken of a single patient's feet. A patient identification mechanism may operate similarly, identifying a correct patient reference image based on a recently acquired image. Images acquired by internal reflection-based image captures systems of embodiments of the present invention may be utilized for a particularly robust verification mechanism due to the high level of fine detail, e.g., ridges, creases, or lined patterns on a foot sole, achievable by internal reflection-based imaging. A patient verification system may match each acquired image to the references by any means, such as by matching geometric features, size, color, or other metrics of a foot image. The verification system may accurately associate images or data with a given patient. This system may prevent false alerts, e.g., due to detection of large changes in foot geometry or color between the feet of two different patients, and also facilitate use a single periodic monitoring device by multiple patients, e.g., increasing ease of use in a clinical setting or multi-patient home.

For example, in one embodiment of the present invention, a monitoring system can be configured to acquire a preliminary internal reflection-based image when a patient steps onto the transmissive sheet. The internal reflection-based image can be compared to a patient reference image to verify or determine the identity of the patient. Additional types of images or data may subsequently be acquired.

Patient verification or identification mechanisms of embodiments of the present invention are not limited to total internal reflection-based images. In one embodiment of the present invention, a reflection image can be analyzed for one or more predetermined metric, including but not limited to the shape of an outline of tissue contacting the transmissive sheet, a length from a first identifiable point on the foot to a second identifiable point on the foot, area occupied by soles of the feet, or any similar such metrics or combinations thereof. Identifying images and any subsequent images acquired by a monitoring device of embodiments of the present invention can be stored to a file, e.g., in the device, external memory or network, server, associated with the identified patient.

Image capture systems in embodiments of the present invention can be activated by one or more of a variety of triggers. In one embodiment of the present invention, a trigger can be manual, e.g., a physical or simulated button a patient can press. For example, a user interface or application can be configured to control the image capture system and thereby activate image capture upon indication by the patient through his or her electronic device, e.g., smart phone, tablet, or similar device. Alternatively, image capture can be initiated through one or a combination of sensors. These sensors can include any type of motion sensor, including but not limited to ultrasonic or microwave motion sensors; heat sensor, including but not limited to passive or active infrared sensors; or weight sensor, e.g., mechanical or electronic strain gauge.

Image capture triggers may be configured to activate an image capture system when a patient's foot is above the transmissive sheet but still unloaded, e.g., not yet in contact or bearing the patient's weight, as well as or instead of once a patient is standing on the sheet. In one embodiment, an initial trigger, e.g., a motion or heat sensor, can activate acquisition of an unloaded image or set of images, while a second trigger, e.g., a strain gauge, can activate acquisition of a loaded image or set of images. Sets of images can be acquired as video, e.g., at 30 fps or 15 fps, or in a burst mode, e.g., 2 pictures/second, 3 pictures/second, 4 pictures/second, 5 pictures/second, 6 pictures/second, 7 pictures/second, 8 pictures/second, and so forth.

Embodiments of the present invention may also comprise measurement systems for tissue temperature, tissue perfusion, patient weight, pulse, respiratory rate, localized pressure, or other metrics or conditions related to tissue and patient health. For example, temperature may be monitored by integration of one or more infrared sources and sensors; permanent or removable thermochromic liquid crystal (LC) sheets; or similar mechanisms.

Temperature may also be monitored by infrared or near-infrared imaging techniques. For example, one embodiment of the present invention can comprise a source or sources configured to emit near-infrared light, e.g., light having wavelengths between 750 nm and 900 nm, 800 nm and 900 nm, or 840 and 860 nm, inclusive, or any wavelength within or between such ranges. This embodiment of the present invention may comprise an additional sensor and lens configured to detect near-infrared light. However, this embodiment may alternatively be configured to allow a shared sensor to image visible and near-infrared image of feet on a transmissive sheet. A lens or system of lenses coupled to said sensor can be tailored in an achromatic, apochromatic, or superachromatic manner to allow two, three, four, or more wavelengths of light, or ranges of light, to be focused on the sensor. Said lens or system of lenses can be tailored to focus one or more visible wavelengths, e.g., between 390 and 700 nm, and one or more near-infrared wavelengths, e.g., between 750 and 900 nm, to a shared focal plane. Such lenses or lens systems may comprise a plurality of elements made of crown glass, flint glass, transparent liquids, or any similar materials.

In another embodiment of the present invention, temperature can be measured by an infrared thermographic camera, e.g., utilizing wavelengths greater than 1 µm. In this embodiment, the transmissive sheet may transmit infrared light. The sheet can, for example, be a plastic or other polymer configured to transmit infrared light. However, such materials may be opaque to visible light. The sheet can also be an optical salt, such as chlorides or bromides, which may transmit both visible and infrared wavelengths. Additional embodiments of the present invention comprising infrared thermographic cameras for temperature information are later described.

Tissue perfusion may be monitored by inclusion of an optical perfusion measurement system. Exemplary optical methods for determination of tissue perfusion can be found in U.S. patent application Ser. No. 13/011,835, entitled "Method and Apparatus for Pressure Sore Detection," herein incorporated by reference in its entirety. Heart rate may be determined via image or video analysis. For example, tissue color differences between successive frames in an acquired video can be analyzed to determine or approximate heart rate. In another embodiment of the present invention, Eulerian video magnification, such as that described by Wu et al. (Hao-Yu Wu, Michael Rubinstein, Eugene Shih, John Guttag, Fredo Durand, William Freeman, Eulerian video magnification for revealing subtle changes in the world, ACM Transactions on Graphics (TOG), v.31 n.4, p. 1-8, July 2012), herein incorporated by reference in its entirety, may be utilized to derive heart rate information from a short video, e.g., series of image acquired by image capture systems of embodiments of the present invention. These and other methods to determine heart rate, temperature information, and similar metrics from image data in embodiments of the present invention can be implemented in microprocessors, chips, or similar elements within the device, or in external processors, cloud computing networks, or similar environments.

Patient weight can be a metric relevant both for overall patient health as well as podiatric health; patient weight can increase the pressure loads experienced by patients' feet during walking and standing. Embodiments of the present invention may comprise a weight measurement system, e.g., such that a patient's weight can be measured in conjunction with any other images or data acquired. A weight measurement system may, for example, comprise one or more strain gauges positioned on the legs, joints, or other elements of device housing. A patient's weight may be displayed, stored, or otherwise utilized for health analysis. A weight measurement system may also optionally serve as a trigger for an image capture system, e.g., as an indicator that a patient has stepped onto the transmissive sheet.

In another embodiment of the present invention, wires, capacitive elements, resistive elements, or similar components may be embedded in the top layer of a transmissive sheet, e.g., such that one or more of the components are in contact with patient tissue. These components may be configured to measure the impedance of patient tissue. Impedance can be measured as an average or total value over the entire foot or feet, or may be measured in localized regions. Impedance can be affected by the moisture content of tissue, and may therefore be indicative of fluid build-up, e.g., edema, or conversely of excessive dryness. Wires and resistive or capacitive elements may also or alternatively be utilized as electrodes for electrocardiography (ECG) measurements, e.g., to determine a patient's pulse.

Wires and resistive or capacitive elements may be connected or configured in a grid-like fashion co-planar with the surface of the transmissive sheet. The components may form one grid, e.g., which may contact both feet, or in two or more grids, e.g., which may each contact one foot or unique regions on each foot. The grid or grids may further serve as fiducial markers for image registration or analysis purposes. Components of the grids may be fine enough as to not significantly occlude the view of tissue in acquired images.

In one embodiment of the present invention, image or data analysis can further comprise determination of an overall foot-health score, rating, or similar metric. This score or rating can be displayed to the patient, such as on an on-device screen, handheld device, computer, or other display. A color, symbol, or other visual cue can be associated with a given rating or range of ratings. The score or rating can be based on or derived from any acquired data or analyses, including but not limited to the detection of unusual tissue color or geometrical features, identification of wounds or irritated tissue, changes from a reference image or prior images, or any other data features.

Images, data, or any analysis results may be automatically transmitted to a medical practitioner or podiatrist, e.g., to an external device, network, server, or similar. In one embodiment, images, data, or analyses can be transmitted to a medical practitioner regularly, e.g., once daily or each time a patient steps on the periodic-monitoring device. This embodiment may be particularly useful for patients with a pre-existing or healing condition on their feet, which a medical practitioner may wish to monitor closely. In an alternative embodiment, images, data, or analyses can be transmitted based on results of an automated screening, e.g., if an overall foot health score or rating meets a predetermined criterion or if an at-risk or injured site is detected in an image. This embodiment may be particularly useful for diabetic patients with no existing ulcers or injuries on their feet but a risk of development due to neuropathy.

In another embodiment of the present invention, a user interface can be configured to allow a patient to elect transmission of images, data, or analyses to his or her medical practitioner. This user interface may be implemented on a device display, personal computer, smart phone, or handheld or other electronic device. The interface may be implemented on the same or a different display than that on which images, scores or ratings, or other information from the monitoring device is displayed. The interface may provide a button or option allowing the patient to transmit images or data to the medical practitioner's receiving unit, e.g., computer, device, or server. The interface may allow a patient to elect transmission of data or to contact a medical practitioner based on raw images or data, or on analyzed results from the device such as an overall health score or detected sites of injury or ulceration risk.

Figure 18:
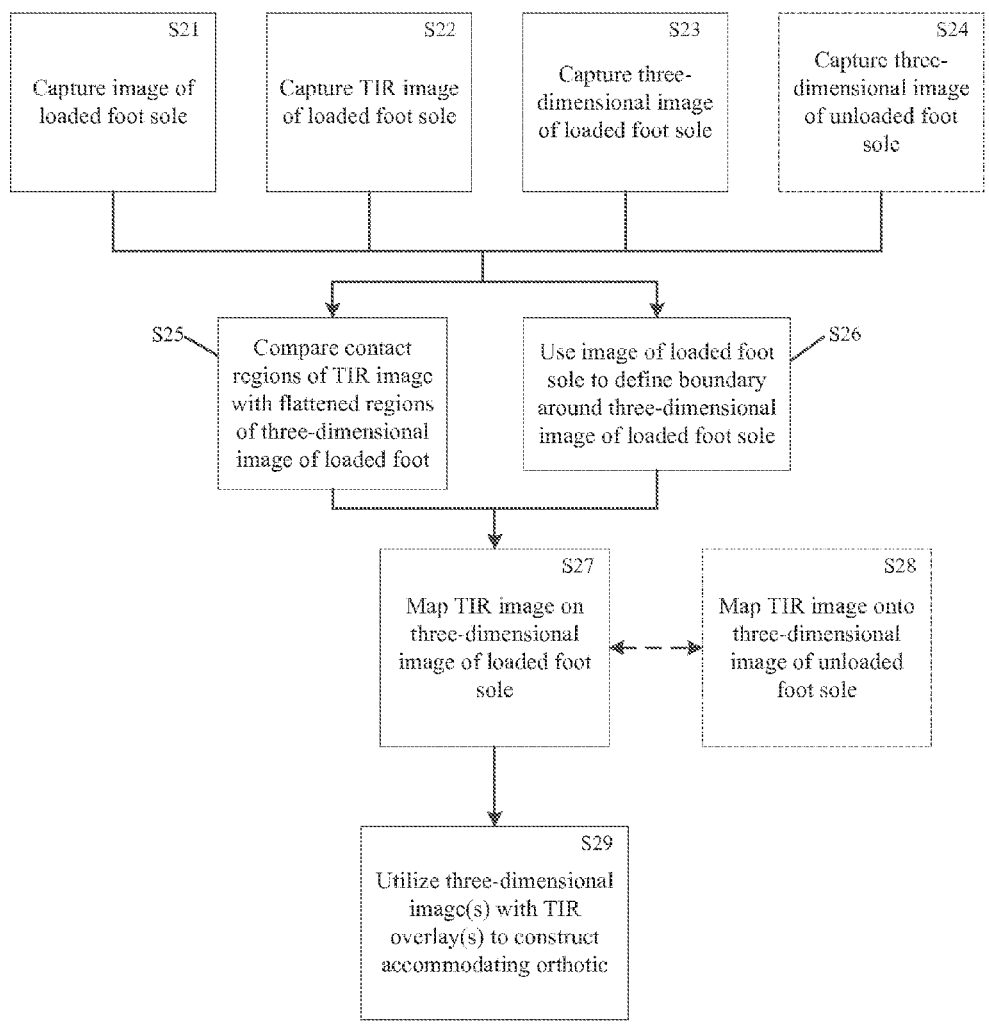
FIG. 18 is a diagram representing a method of acquiring data and constructing a model for an orthotic of one embodiment of the present invention.

FIG. 18 is a diagram representing a method of acquiring data and constructing a model for an orthotic of one embodiment of the present invention. A first series of steps can comprise capturing a visible light image (S21), TIR image (S22), and three-dimensional image (S23) of a loaded foot. Methods of capturing these three image types with a single, compact device have been described herein; any such methods or combinations thereof can be utilized. Optionally, a three-dimensional image of an unloaded foot can also be captured (S24). Step S24, e.g., capture of an unloaded foot image, can also be accomplished with devices of embodiments that have been described. For example, instructions or queues for a patient to hold a foot slightly above a sheet or surface while standing on or near the device can be provided, such that an unloaded image can be captured. Alternatively, a motion, heat, or similar sensor can initiate image capture as a patient steps onto the device, such that an image can be captured before the foot is loaded.

In a further step S26, a visible-light image, e.g., as acquired in step S21, may be utilized to define foot boundaries in a three-dimensional image of a loaded foot sole, e.g., from step S23. Pressure points on a loaded foot can begin to be identified in a step S25 of comparing relatively flat tissue regions in the three-dimensional image with bright spots of the TIR image. Significant mismatches between bright regions of the TIR image and flat regions of the three-dimensional image can also serve as a possible indication of error in the image capture process. In one embodiment of the present invention, a predetermined amount of disagreement or offset between bright regions in the TIR image and flattened regions in the three-dimensional image can trigger a user notification to retake the image series, e.g., to repeat steps S21 through S23 to ensure proper registration between image types.

In a related step S27, a TIR image can be mapped onto a three-dimensional image of the loaded foot sole, and optionally onto a three-dimensional image of an unloaded foot sole (S28). The resultant composite image or images can represent the shape and configuration of a patient's foot when standing or at rest and the relative amounts of pressure applied to various regions. Relative pressures, e.g., from TIR brightness, may be quantified or converted to absolute values by calculating total pressure the foot or feet bear under a patient's weight, and assigning increments of the total pressure to foot regions according to TIR patterns. The patient's weight may be obtained from an external record, or may be measured by the imaging device, e.g., by use of strain gauges or other mechanisms that have been described. A custom orthotic can be designed using the shape and pressure point information from the image or images of step S27 and optionally step S28 (S29). The custom orthotic may be configured to support the patient's foot in a manner that relieve pressure points or other regions at risk of ulcer development. In other embodiments of the present invention, information from visible light images, including but not limited to presence of nonblanchable erythema, calluses, open wounds, or similar features can also be utilized in the orthotic design.

Embodiments of the present invention may also be operable without use of a solid transmissive sheet, e.g., a glass or other optically transparent sheet. Such embodiments may provide a surface or area in order to support a patient's feet or indicate a plane in which the feet should be positioned during image capture. The surface can be load bearing, e.g., configured to bear a patient's weight, or non-load bearing, e.g., configured for a patient to rest his or her feet such as from a chair. Transparent or opaque wires, meshes, plastics, fibers, or any similar such materials or combinations thereof can form such surfaces. The wires, plastics, fibers, or other meshes or materials can be constructed in a manner to allow a substantial portion of the patient's feet to be viewed from below without obstruction; the wires, plastics or fibers can be relatively thin, positioned with substantial spacing between neighboring elements, or have similar such configurations. These embodiments may be less costly to manufacture than embodiments having a glass transmissive sheet and may also accommodate a number of alternative imaging modalities.

In one embodiment of the present invention, a thermographic camera, e.g., utilizing wavelengths between 1 µm and 14 µm, can be incorporated in a foot imaging device, e.g., in conjunction with a visible light imaging system or other imaging modalities. The thermographic camera can provide an accurate temperature map of foot tissue, and may be analyzed independently or combined with other images and information available from the device, such as visible images. A high resolution thermographic camera, such as a thermographic camera having 32×32, 80×80, 140×140, 320×240, or more pixels can be utilized. Alternatively, a relatively low resolution thermographic camera can be utilized. For example, a thermographic camera having 4×4, 8×8, 10×10, or a similar number of pixels can be utilized. In this embodiment, the resolution of thermographic images that are acquired can be significantly improved using an image acquired from a slightly offset visible light camera. One such super-resolution technique is described by Chikamatsu et al. (Chikamatsu, S.; Nakaya, T.; Kouda, M.; Kuroki, N.; Hirose, T.; Numa, M., "Super-resolution technique for thermography with dual-camera system," Proceedings of 2010 IEEE International Symposium on Circuits and Systems (ISCAS), pp. 1895,1898, May 30, 2010-Jun. 2, 2010), herein incorporated by reference in its entirety.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A device for monitoring a foot of a human patient, said device comprising:
    a transmissive sheet configured to bear a load of at least 90 kg with at least 250 cm$^2$ of surface;
    a housing configured to support said transmissive sheet at a height of no more than 23 cm above a bottom of the housing and to bear said load of at least 90 kg;
    a foot image capture system positioned below said transmissive sheet and within said housing, having a first diffuse optical light source and a first optical image sensor and configured to capture a field of view including at least 250 cm$^2$ of surface of said transmissive sheet;
    a second light source, wherein light emitted from said second light source is totally internally reflected within said transmissive sheet without contact by said foot and wherein contact of said foot on said transmissive sheet causes said light from said second light source to be reflected out of said transmissive sheet toward said first optical image sensor;
    a first polarizer positioned to polarize light emitted from said first diffuse optical light source;
    a second polarizer positioned in front of said first optical image sensor, wherein said first polarizer creates a first type of polarization and said second polarizer creates a second type of polarization that cancels light that has undergone specular reflection due to reflection by said transmissive sheet rather than diffuse reflection due to reflection by said foot;
a third near infrared light source configured to emit light with a wavelength between 750 nm and 900 nm; and
a lens configured to focus light of at least two unique wavelengths, of which a first wavelength is between 390 nm and 710 nm and a second wavelength is between 750 nm and 900 nm, to a single focal plane.

2. The device of claim 1 further comprising:
an array of a second optical image sensor and a third optical image sensor below said transmissive sheet;
lenses coupled to each of said second and third optical image sensors configured to focus unique predetermined portions of said field of view onto said second and third optical image sensors and limit overlap between image sets of said second and third optical image sensors to less than 25 percent; and
a processing unit configured to construct a final image of said field of view from said unique predetermined portions.

3. The device of claim 1 further comprising:
a central support below a central point of said transmissive sheet configured to support a rotating element, wherein said first optical image sensor is coupled to said rotating element, and said rotating element is configured to rotate said optical image sensor between a first position and a second position;
a first outer angled mirror below said transmissive sheet and within said housing configured to reflect an image of a first half of said field of view inward onto said optical image sensor in said first position; and
a second outer angled mirror below said transmissive sheet and within said housing opposite said first outer angled mirror configured to reflect a second half of said field of view inward onto said optical image sensor in said second position.

4. The device of claim 1 further comprising:
a central support below a central point of said transmissive sheet configured to support said first optical image sensor in a first position and a second optical image sensor in a second position;
a first outer angled mirror below said transmissive sheet and within said housing configured to reflect an image of a first half of said field of view inward onto said first optical image sensor in said first position; and
a second outer angled mirror below said transmissive sheet and within said housing opposite said first outer angled mirror configured to reflect a second half of said field of view inward onto said second optical image sensor in said second position.

5. The device of claim 1 wherein said transmissive sheet comprises glass without anti-reflection treatment.

6. The device of claim 1 further comprising a wireless transmitter for transmitting image data from said device to an external location.

7. The device of claim 1 wherein said transmissive sheet is further positioned at a height less than 5 cm above a step surface and said image capture system is positioned below said step surface.

8. The device of claim 1 wherein said second light source is coupled to a prism that is coupled to said transmissive sheet, wherein light emitted by said second light source is directed onto one side of said prism and wherein said prism directs said light from said second light source into said transmissive sheet.

9. A device for monitoring feet of a human patient, said device comprising:
a transmissive sheet configured to accommodate soles of said feet and to bear a load of at least 90 kg;
a first optical sensor positioned no more than 23 cm below said transmissive sheet;
a first diffuse optical light source;
a second light source, wherein light emitted from said second light source is totally internally reflected within said transmissive sheet without contact by said feet and wherein contact of said feet on said transmissive sheet causes said light from said second light source to be reflected out of said transmissive sheet toward said first optical image sensor, wherein said second light source is coupled to a prism that is coupled to said transmissive sheet, wherein light emitted by said second light source is directed onto one side of said prism and wherein said prism directs said light from said second light source into said transmissive sheet;
a central reflective element positioned under said transmissive sheet directly above said optical sensor;
a first outer mirror below the transmissive sheet configured to reflect a first field of view of at least 250 cm$^2$ from said transmissive sheet toward a first side of said central reflective element and onto one-half of said optical sensor;
a second outer mirror below the transmissive sheet configured to reflect a second field of view of at least 250 cm$^2$ from said transmissive sheet toward a second side of said central reflective element and onto the other half of said optical sensor so that said optical sensor simultaneously acquires said first field of view and said second field of view as a single image;
a first lens coupled to said optical sensor configured to focus said first field of view and said second field of view reflected from said central reflective element onto said optical sensor;
a third near infrared light source configured to emit light with a wavelength between 750 nm and 900 nm; and
a second lens configured to focus light of at least two unique wavelengths, of which a first wavelength is between 390 nm and 710 nm and a second wavelength is between 750 nm and 900 nm, to a single focal plane.

10. The device of claim 9 wherein said transmissive sheet is disposed at an angle relative to said first outer mirror, wherein said angle is between 8 degrees and 45 degrees, inclusive.

11. The device of claim 9 wherein said transmissive sheet is disposed at an angle relative to said first outer mirror, wherein said angle is less than 40 degrees.

12. The device of claim 9 wherein said first field of view and said second field of view are separated by at least 10 cm.

13. The device of claim 9 further comprising a support structure configured to fix optical distance between said central reflective element and said lens.

14. A method for monitoring feet of a human patient, said method comprising:
automatically capturing visible-light images of soles of said feet upon said patient standing on a transmissive sheet with an optical sensor located no more than 20 cm below said transmissive sheet, wherein said optical sensor is shielded against light that has undergone specular reflection due to reflection by said transmissive sheet rather than diffuse reflection due to reflection by said feet;

automatically capturing total internal reflection (TIR) images of said soles upon patient standing on said transmissive sheet using TIR imaging;

transmitting said visible-light images and said TIR images to a database accessible by a medical professional;

comparing flat regions of said visible-light images and bright regions of said TIR images to identify pressure points on said feet and an error in capturing said visible-light images and said TIR images;

associating said images of said soles with said patient in said database according to a predetermined characteristic;

automatically capturing additional images with near-infrared light of said soles upon said patient standing on said transmissive sheet and transmitting said additional images to said database.

15. The method of claim 14 further comprising:

capturing an image of said transmissive sheet without said patient standing on said transmissive sheet; and subtracting features appearing in said image of said transmissive sheet from said visible-light images and from said TIR images.

16. A device for monitoring a foot of a human patient, said device comprising:

a transmissive sheet configured to bear a load of at least 90 kg with at least 250 cm$^2$ of surface;

a housing configured to support said transmissive sheet at a height of no more than 23 cm above a bottom of the housing and to bear said load of at least 90 kg;

a foot image capture system positioned below said transmissive sheet and within said housing, having a first diffuse optical light source and a first optical image sensor and configured to capture a field of view including at least 250 cm$^2$ of surface of said transmissive sheet;

a second light source, wherein light emitted from said second light source is totally internally reflected within said transmissive sheet without contact by said foot and wherein contact of said foot on said transmissive sheet causes said light from said second light source to be reflected out of said transmissive sheet toward said first optical image sensor;

a first polarizer positioned to polarize light emitted from said first diffuse optical light source;

a second polarizer positioned in front of said first optical image sensor, wherein said first polarizer creates a first type of polarization and said second polarizer creates a second type of polarization that cancels light that has undergone specular reflection due to reflection by said transmissive sheet rather than diffuse reflection due to reflection by said foot and an air flow system configured to generate a flow of air across said transmissive sheet and remove moisture from said transmissive sheet.

* * * * *